(12) United States Patent
Aiko et al.

(10) Patent No.: US 9,164,042 B2
(45) Date of Patent: Oct. 20, 2015

(54) DEVICE FOR DETECTING FOREIGN MATTER AND METHOD FOR DETECTING FOREIGN MATTER

(75) Inventors: Kenji Aiko, Ninomiya (JP); Shigeya Tanaka, Hitachi (JP); Yasuko Aoki, Mito (JP); Hiroshi Kawaguchi, Hitachinaka (JP); Kei Shimura, Mito (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 28 days.

(21) Appl. No.: 13/984,286

(22) PCT Filed: Feb. 1, 2012

(86) PCT No.: PCT/JP2012/052206
§ 371 (c)(1),
(2), (4) Date: Aug. 8, 2013

(87) PCT Pub. No.: WO2012/108306
PCT Pub. Date: Aug. 16, 2012

(65) Prior Publication Data
US 2013/0320216 A1    Dec. 5, 2013

(30) Foreign Application Priority Data

Feb. 10, 2011 (JP) .................................. 2011-026884

(51) Int. Cl.
*G01N 21/88* (2006.01)
*G01B 11/30* (2006.01)
(Continued)

(52) U.S. Cl.
CPC .............. *G01N 21/88* (2013.01); *G01B 11/303* (2013.01); *G01N 21/3581* (2013.01);
(Continued)

(58) Field of Classification Search
CPC .......... G01N 21/3563; G01N 21/3581; G01N 21/55; G01N 21/88
USPC ......................................................... 250/349
See application file for complete search history.

(56) References Cited

U.S. PATENT DOCUMENTS

| | | |
|---|---|---|
| 5,861,952 A | 1/1999 | Tsuji et al. |
| 6,191,849 B1 | 2/2001 | Maeshima et al. |

(Continued)

FOREIGN PATENT DOCUMENTS

| | | | |
|---|---|---|---|
| JP | 55082022 A | * | 6/1980 |
| JP | 4-194736 | | 7/1992 |

(Continued)

OTHER PUBLICATIONS

Office Action in Korean Patent Appln. 10-2013-7021025, mailed Jun. 27, 2014 (in Korean, 7 pgs.; English language translation, 9 pgs.).

(Continued)

*Primary Examiner* — Marcus Taningco
(74) *Attorney, Agent, or Firm* — Baker Botts L.L.P.

(57) ABSTRACT

The present invention provides a device for detecting foreign matter and a method for detecting foreign matter to detect a foreign matter on a surface of an object such as a film of an electrode mixture etc. or a foreign matter contained in the object, thereby to improve the reliability of the object. By irradiating an object with a terahertz illumination light 100 (wavelength of 4 μm to 10 mm) and detecting a scattered light 660 from an electrode 10 as an example of the object by a scattered light detector 200, a foreign matter on a surface of the electrode 10 or contained in the electrode 10, for example, a metal foreign matter 720, is detected. The electrode 10 is one in which electrode mixture layers 700 each including an active material 701, conductive additive and a binder as components are coated on both surfaces of a collector 710. The scattered light 660 results from a part of a transmitted light 656 reflected by the metal foreign matter 720.

21 Claims, 14 Drawing Sheets

(51) Int. Cl.
*G01N 21/3581* (2014.01)
*G01N 21/94* (2006.01)
*H01M 4/04* (2006.01)
*H01M 4/139* (2010.01)
*G01N 21/3563* (2014.01)

(52) U.S. Cl.
CPC ............ *G01N 21/8806* (2013.01); *G01N 21/94* (2013.01); *H01M 4/0404* (2013.01); *H01M 4/139* (2013.01); *G01N 21/3563* (2013.01); *Y02E 60/122* (2013.01)

(56) References Cited

U.S. PATENT DOCUMENTS

| | | | |
|---|---|---|---|
| 2006/0043298 A1* | 3/2006 | Kawase et al. | 250/339.06 |
| 2007/0138392 A1* | 6/2007 | Cole | 250/341.1 |
| 2009/0189078 A1 | 7/2009 | Itsuji | |
| 2010/0195090 A1* | 8/2010 | Ohtake | 356/51 |
| 2010/0235114 A1* | 9/2010 | Levy et al. | 702/40 |

FOREIGN PATENT DOCUMENTS

| | | |
|---|---|---|
| JP | 6-201601 | 7/1994 |
| JP | 06-331559 | 12/1994 |
| JP | 8-297086 | 11/1996 |
| JP | 11-190702 | 7/1999 |
| JP | 2001-66375 | 3/2001 |
| JP | 2001-141647 | 5/2001 |
| JP | 2005-172774 | 6/2005 |
| JP | 2005-214758 | 8/2005 |
| JP | 2006-71412 | 3/2006 |
| JP | 2006-78426 | 3/2006 |
| JP | 2007-199044 | 8/2007 |
| JP | 2008-26190 | 2/2008 |
| JP | 2009-204605 | 9/2009 |
| JP | 2009-300279 | 12/2009 |
| JP | 2010-19647 | 1/2010 |
| WO | WO 2006/085403 A1 | 8/2006 |

OTHER PUBLICATIONS

Houshmand, Kaveh. 'Defect Detection Via Thz Imaging: Potentials and Limitations.' 2008. Masters Thesis, University of Waterloo, Ontario, Canada. [68 pages].

Siegel, Peter H. et al, 'Terahertz Heterodyne Imaging, Part II: Instruments.' International Journal of Infrared and Millimeter Waves, vol. 27, No. 5, May 2006, pp. 631-655.

Office Action in Japanese Patent Application 2012-556835, mailed Dec. 24, 2013, (in Japanese, 3 pages); [partial English language translation, 5 pages].

Office Action in Japanese Patent Application 2012-556835, mailed Apr. 8, 2014, (in Japanese, 4 pages); [partial English language translation, 6 pages].

Optical Constants of Water ($H_2O$) Http://refractiveindex.info/ : Mar. 11, 2013.

* cited by examiner

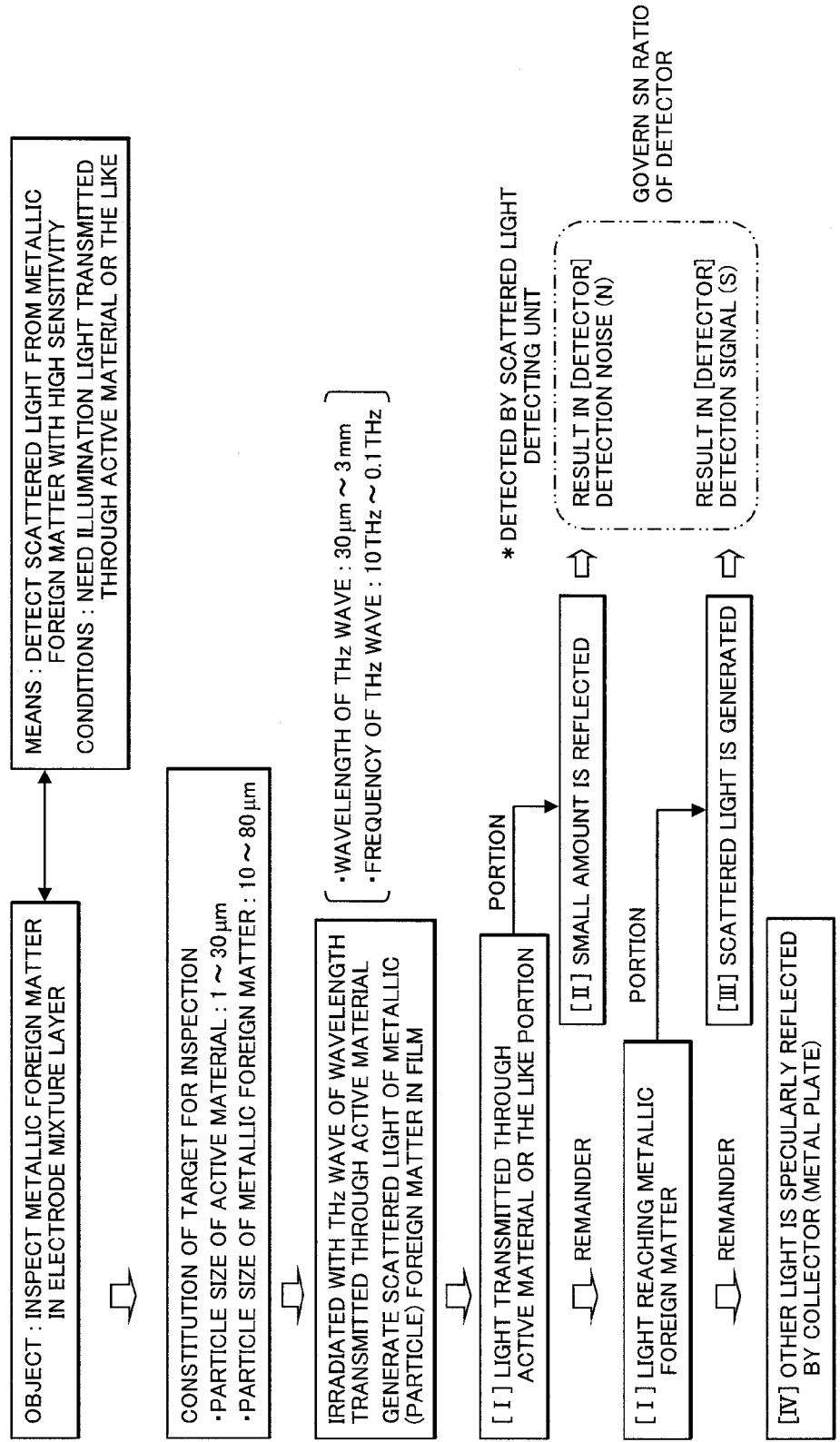

DEVICE FOR DETECTING FOREIGN MATTER AND METHOD FOR DETECTING FOREIGN MATTER

TECHNICAL FIELD

The present invention relates to a device for detecting foreign matter and a method for detecting foreign matter, and particularly to a device for detecting foreign matter and a method for detecting foreign matter both using far-infrared rays or the like.

BACKGROUND ART

A lithium ion battery (LIB) has rapidly been growing in demand in recent years.

However, a problem remains in that each fine metal foreign matter is mixed into the battery in a production of the LIB. There has therefore been a demand for an increase in a detection accuracy of the metal foreign matter in the production process.

In general, as means to detect a foreign matter of micro size attached to a surface of a semiconductor wafer, a liquid crystal substrate or the like with high sensitivity, there has been used a method for detecting scattered light using a dark field configuration (DF configuration).

An electrode sheet being one of members of the LIB is one that an electrode mixture being a mixture containing an active material, a conductive additive and a binder has been coated on a metal foil being a collector. In an inspection of the foreign matter mixed in the film of the electrode mixture in its production process, there has been a demand for the detection of a metal foreign matter of small size (several micrometers or so) contained in the film with high sensitivity. Among battery materials, a positive electrode material is generally used as a component, such as $LiCoO_2$ or the like being a few micrometers in a particle size and being several tens of micrometers at the same level as the thickness. Therefore, a transmittance of visible light becomes 0.1% or less. It is thus difficult to detect the foreign matter in the film by using the visible light.

Patent Document 1 discloses an inspection method of a paper sheet or the like, the method including the steps of irradiating the paper sheet or the like with terahertz light with a wavelength of 50 μm to 2 mm, detecting the terahertz reflected light reflected by front and back surfaces of the sheet or the like, and detecting an intensity of an interference due to a phase difference of the detected terahertz reflected light to detect a thickness of the sheet or the like.

Patent Document 2 discloses an apparatus of real-time terahertz tomography and terahertz spectral imaging, in which a technique for using a THz pulse and probe pulse light as a non-common axis and measuring a terahertz time waveform in a single shot and further irradiating an object to be measured with the THz pulse in a line condensing state and making unnecessary a scanning mechanism by using a two-dimensional imaging device as a detector with an objective of realizing a complete real-time measurement.

Patent Document 3 discloses a defect inspecting apparatus which changes the polarization axis of a polarizer according to the specific polarization axis of an object to be inspected and polarizing light from illuminating means to irradiate the object with the light and in which an analyzer aligns the polarization axis with the polarization axis of the polarizer and detects a change in penetration amount or a change in the reflection amount by optical detecting means through the transmitted light from the object or the reflected light, thereby detecting defects of the object.

Patent Document 4 discloses a surface inspecting apparatus which uses a microwave having a wavelength of 10 μm to 1 mm to detect a reflected wave from a target surface to be measured, thereby determining the surface shape of a metal.

Patent Document 5 discloses an inspection method which allows the infrared sufficiently longer in wavelength than the diameter of powder particles to pass through the inside of the power particles to thereby examine an internal structure of a subject constructed by aggregating the powder particles.

Patent Document 6 discloses an apparatus which irradiates an object to be inspected with a pulse-shaped or continuous sub terahertz electromagnetic wave having a wavelength of 600 μm to 3 mm (0.5 THz to 100 GHz), and performs an inspection of a foreign matter in powder particles by utilizing a difference in a propagation time or a difference in a transmittance due to its substance.

In Non-Patent Document 1, wavelength dependences of refractive indices and absorption coefficients of various metals, composite oxide or the like are described.

PRIOR ART DOCUMENT

Patent Documents

Patent Document 1: Japanese Patent Laid-Open No. 2009-300279
Patent Document 2: WO2006/085403 (Japanese Patent Application No. 2007-502543)
Patent Document 3: Japanese Patent Laid-Open No. 2006-78426
Patent Document 4: Japanese Patent Laid-Open No. 2005-214758
Patent Document 5: Japanese Patent Laid-Open No. 2001-141647
Patent Document 6: Japanese Patent Laid-Open No. 2001-66375

Non-Patent Documents

Non-Patent Document 1: http://refractiveindex.info/

SUMMARY OF THE INVENTION

Problems that the Invention is to Solve

In a region between a visible light having a wavelength of about 400 to 700 nm and an infrared light having a wavelength of near 1 μm, most of the light irradiated to the film of the electrode mixture is absorbed. Further, the influence of scattering by active material particles is large in a region of a near infrared having a wavelength of a few micrometers, and thus the light irradiated cannot be transmitted.

An object of the present invention is to detect a foreign matter on a surface of an object, such as a film of an electrode mixture etc., or a foreign matter contained in the object, thereby to improve the reliability of the object.

Means for Solving the Problems

The present invention is characterized by irradiating an object with an illumination light having a wavelength of 4 μm to 10 mm, and detecting a scattered light from the object as a signal, thereby detecting a foreign matter on a surface of the object or contained in the object.

Effects of the Invention

According to the present invention, an illumination light having a wavelength of 4 μm to 10 mm is applied to an object, and a scattered light from the object is detected as a signal, thereby making it possible to detect foreign matter on a surface of the object and contained in the object and improve a reliability of the object.

BRIEF DESCRIPTION OF THE DRAWINGS

FIG. 1 is a flow diagram showing an overview of a method of detecting foreign matter mixed in an electrode mixture layer of a lithium ion secondary battery.

MODE FOR CARRYING OUT THE INVENTION

Figure 2A:
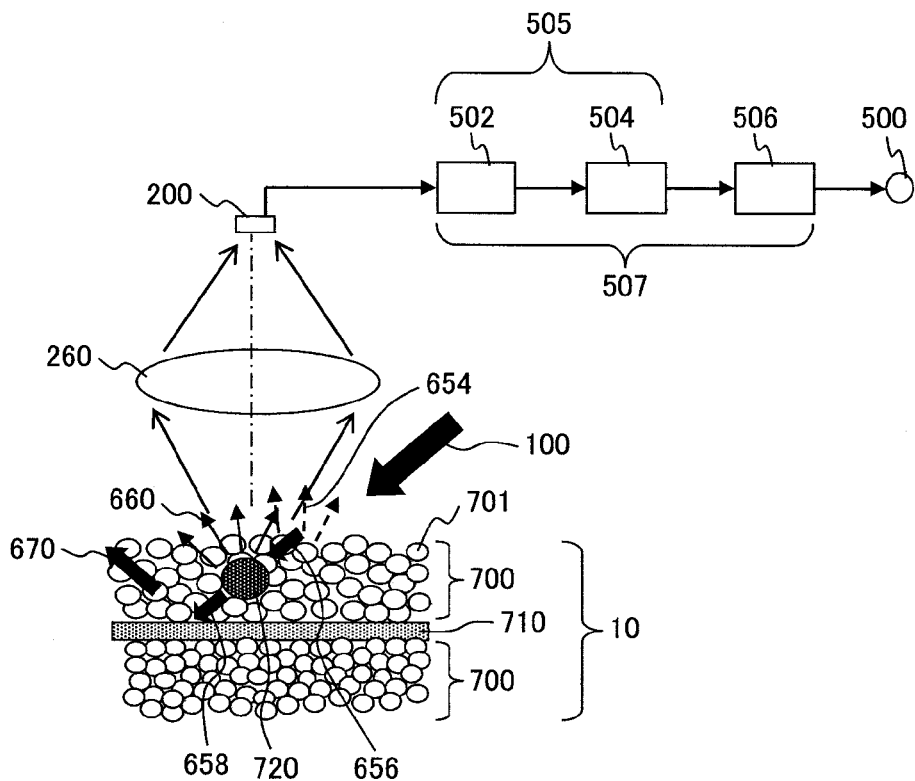
FIG. 2A is a typical diagram showing a principle of scattering of a terahertz wave.

As an object, the present invention relates particularly to a detecting device and method for detecting heterologous foreign matter (such as a metal) mixed in a multi-particle structure (an electrode mixture layer, etc.) formed of particles that pass through a far infrared ray or the like.

When a terahertz wave transmitted through a composite oxide of an active material or the like is used as illumination light and applied to an electrode material film (an electrode mixture layer) including a metal foreign matter as a target object with a DF configuration, a scattered light (a light irregularly reflected by the terahertz waves transmitted through the composite oxide being applied to the metal foreign matter) is generated from the metal foreign matter. It is possible to detect a foreign substance or matter by detecting the scattered light. That is, when terahertz waves belonging to the far infrared rays are used, the influence of scattering by active material particles is reduced, the transmittance also becomes several tens of percent, and the scattered light from the metal foreign matter in the film can be detected.

Preferably, the scattered light can efficiently be detected by placing over the electrode material film, a scattered light detection optical system for capturing the scattered light.

A description will hereinafter be made of a device for detecting foreign matter and a method for detecting foreign matter according to one embodiment of the present invention.

Incidentally, in the present specification, the device for detecting foreign matter is also called a foreign matter inspecting apparatus, and the method for detecting foreign matter is also called a foreign matter inspecting method respectively.

The device for detecting foreign matter is a device for detecting foreign matter that detects foreign matter on the surface of an object or in the object, which is characterized in that it includes an illumination light generating unit which generates illumination light applied to the object, and a scattered light detecting unit which detects scattered light from the object as a signal, using a light receiving element, and that the wavelength of the illumination light ranges from 4 μm to 10 mm. Incidentally, the foreign matter contained in the surface of the object or the object is intended to include not only foreign matter contained in the surface of the object or the object, but also foreign matter contained in the surface of the object and the object.

Here, the scattered light is intended to include the light scattered in the course of the illumination light being transmitted through the object, and the light diffusely reflected by the foreign matter contained in the object.

Preferably, the device for detecting foreign matter further includes a specular reflection light detecting unit which detects the specular reflected light from the object by using a light receiving element.

Here, the specular reflected light refers to light that is reflected at the same angle as the illumination light elevation angle being an angle at which the illumination light is incident on the object. However, it is intended to include light that is within the range of an angular aperture of an optical system in detecting specular reflected light.

Preferably, further, the device for detecting foreign matter further includes a smoothing processing unit which smoothes the signal obtained by the scattered light detecting unit, and a filter processing unit that filters the smoothed signal smoothed in the smoothing processing unit.

Preferably, the device for detecting foreign matter further includes a manifestation processing unit which performs differential processing of a noise removal signal obtained by the filter processing unit.

Preferably, the device for detecting foreign matter further includes a heterodyne for processing signals obtained in at least one of the scattered light detecting unit and the specular reflection light detecting unit, and a lock-in amplifier.

Preferably, the device for detecting foreign matter further includes a synchronous detecting unit which processes a signal obtained by at least one of the scattered light detecting unit and the specular reflection light detecting unit, and a lock-in amplifier.

Preferably, the device for detecting foreign matter further includes a non-linear crystal device which converts the wavelength of at least one of scattered light and specular reflected light. At least one of the scattered light detecting unit and the specular reflection light detecting unit includes an infrared and visible light detector.

Preferably, in the device for detecting foreign matter, an illumination light generating unit includes a combination of femtosecond pulsed laser and a photoconductive antenna InGa electrostrictive element, a combination of nanosecond pulsed laser and a non-linear crystal device, Quantum cascade laser that generates a terahertz wave, a Schottky barrier diode that generates a terahertz wave, a Gunn diode or a TUNNETT diode.

Preferably, in the device for detecting foreign matter, the wavelength of the terahertz wave ranges from 4 μm to 10 mm.

Preferably, the device for detecting foreign matter further includes a focal distance adjusting unit which adjusts the focal lengths of the scattered light and specular reflected light.

Preferably, in the device for detecting foreign matter, at least one of the scattered light detecting unit and the specular reflection light detecting unit includes a one-dimensional sensor or two-dimensional sensor in which a plurality of sensors are arranged.

Preferably, the device for detecting foreign matter further includes an analyzing unit which performs from the signal obtained by the specular reflection light detecting unit, the calculation of the thickness of the object or the depth of the foreign matter contained in the object, or the analysis of components of the foreign matter or the detection of moisture contained in the object.

The method for detecting foreign matter is a method for detecting foreign matter for detecting foreign matter in the surface of the object or the object, which is characterized in that it includes a step of irradiating the object with illumination light, and a step of detecting as a signal, the scattered light from the object and that the wavelength of the illumination light ranges from 4 μm to 10 mm.

Preferably, the method for detecting foreign matter further includes a step of smoothing the signals of the scattered light to perform filtering thereof.

Preferably, the method for detecting foreign matter further includes a step of differential processing each signal obtained by filtering.

Preferably, the method for detecting foreign matter further includes a step of detecting the specular reflected light from the object.

Preferably, the method for detecting foreign matter further includes a step of converting a wavelength of at least one of scattered light and specular reflected light.

Preferably, the method for detecting foreign matter further includes a step of adjusting the focal lengths of the scattered light and specular reflected light.

Preferably, the method for detecting foreign matter further includes a step of performing from the signal obtained by detecting the specular reflected light, the calculation of the thickness of the object or the depth of the foreign matter contained in the object, or the analysis of components of the foreign matter or the detection of moisture contained in the object.

Embodiments of the present invention will be described below with reference to the drawings.

FIG. 1 shows an overview of a method for detecting a metal foreign matter buried in an electrode mixture layer of a lithium ion secondary battery (LIB).

For the purpose of performing with high sensitivity, the detection of foreign matter (hereinafter also called metal foreign matter) of metal particles or the like buried in the electrode mixture layer as an object, a method for detecting scattered light from the metal foreign matter is an effective means. This method needs, as the conditions, the illumination light (electromagnetic wave) that passes through the active material contained in the electrode mixture layer.

The particle size of the active material used for the electrode of the LIB is about 1 to 30 μm range. In contrast, the particle size of the metal foreign matter targeted for detection is in the range of 10 μm at the same level as the active material to 80 μm being the thickness (film thickness) of the common mixture layer. As a typical example, there is mentioned the case where the particle size of the active material is about 10 μm and the particle size of the metal foreign matter is about 30 μm. However, since the particle size of the metal foreign matter targeted for detection depends on the film thickness or the particle size of the active material, it is not limited to the above range, and, for example, the particle size of the metal foreign matter subject to detection may be any detectable range of foreign matter such as metal particles mixed in the collection of particles passing through the far infrared rays.

In the present figure, the path of the illumination light irradiated to the object is classified into four. That is, they are [I] light transmitted through the active material (electrode mixture layer) and reaching the metal foreign matter, [II] light which is a part of the illumination light and is reflected by the upper surface of the active material (electrode mixture layer), [III] light reflected and scattered at the surface of the foreign matter, and [IV] light passing through the active material (electrode mixture layer) and specularly reflected by the collector (metal plate).

If the scattered light from the foreign matter can be generated using the illumination light having a wavelength that passes through the active material under such conditions, it is possible to detect the scattered light from metal particles (metal foreign matter) in the active material. The scattered light from the metal particles becomes a signal S when it enters the scattered light detecting unit.

On the other hand, when the reflected light from the active material enters the scattered light detector, the reflected light becomes an unwanted signal (noise N). As will be described later, when the particles become small in size, the signal S is reduced, and distinguishing the reflected and scattered light from the active material from the signal (noise N) becomes difficult. In this case, preferably, it is preferable to reduce the noise N that decreases the foreign matter detection sensitivity included in the scattered light from the active material.

In a preferred embodiment for reducing the noise N, when the metal particles are detected, the detection signal ratio capable of being taken out from the scattered light detecting unit, that is, the ratio of S/N is preferably used as a condition for determining the sensitivity of detection. The light that is not reflected from the metal particles in the above is further specularly reflected by the collector after passing through the active material. It has been devised in such a way that the specular reflected light is not normally detected. For example, the scattered light detector is placed so as not to detect the specular reflected light.

In the case of an electromagnetic wave long in wavelength, it generally has a property that the transmittance of the material becomes high. Therefore, the electromagnetic wave having a wavelength of several tens of times the particle diameter becomes the condition of the illumination light for scattered light detection. In the case of the LIB, each of electromagnetic waves (wavelength several hundred micrometers) each having a wavelength of about 10 times the size (particle size) of the active material is included in the region from a wavelength band of far-infrared rays to a wavelength band called terahertz wave. It can be a candidate of the illumination light when the foreign matter detection is conducted by the scattered light detection method.

In general, the terahertz wave refers to electromagnetic waves before and after a frequency 1 THz (wavelength 300 µm) and refers to a frequency band of 0.1 THz to 10 THz (wavelength 30 µm to 3000 µm (3 mm)) or a frequency band of frequency 0.3 THz to 3 THz (wavelength 100 µm to 1000 µm (1 mm)).

Even when the particle sizes of the active material and the foreign matter are different from the particle size of the above, it can be estimated that by varying the wavelength, a similar phenomenon and effects are established. For example, if the particle size is from the order of sub micrometers to several micrometers, far-infrared light (wavelength: 4 µm to 100 µm) can be applied. Further, when the particle size is several hundred micrometers to 1 mm, a millimeter-wave (wavelength: 1 mm to 10 mm) is effective. Thus, when a similar effect can be expected even if the wavelength is varied, in this specification, the terms "terahertz wave" or "terahertz illumination light" is used as a term that also includes a region of the above infrared light and millimeter-wave.

FIG. 2A is a typical diagram showing the principle of scattering of each terahertz wave and shows the case of applying a terahertz wave to the electrode of the LIB.

In the present figure, the electrode 10 is one in which electrode mixture layers 700 each including, as components, an active material 701, conductive additive and a binder are coated on both surfaces of a collector 710 (usually a metal foil). There is a case where metal foreign matter 720 is mixed into the electrode mixture layer 700. A detection optical unit 260 and a scattered light detector 200 each constituted by a condensing lens or the like are placed above the electrode 10.

When terahertz illumination light 100 (also called terahertz wave, and also denoted as THz wave) is applied to the electrode 10 obliquely, transmitted light 656 passing through the electrode mixture layer 700 and reflected light 654 reflected at the upper surface of the electrode mixture layer 700 are generated. Then, a part of the transmitted light 656 is reflected by the metal foreign matter 720 and becomes scattered light 660. Transmitted light 658 that has not been applied to the metal foreign matter 720 is reflected by the collector 710 and becomes specular reflected light 670. The scattered light 660 is condensed by the detection optical unit 260 and detected by the scattered light detector 200.

Incidentally, as an example of a light source (illumination light generating unit) for generating the terahertz illumination light 100, there are mentioned a combination of femtosecond pulsed laser and a photoconductive antenna InGa electrostrictive element, a combination of nanosecond pulsed laser and a transducer (non-linear crystal device) formed of anon-linear crystal, quantum cascade laser (QCL) for generating a terahertz wave, a Schottky barrier diode (SBD) for generating a terahertz wave, a Gunn diode, a TUNNETT diode, etc.

A scattered light signal that was detected by the scattered light detector 200 and became an electrical signal is sent to the signal converting section 507 which removes noise. Usually, the scattered light signal is detected as a potential difference. The signal converting section 507 is provided with a noise processing section 505 which receives the scattered light signal and processes the noise N contained in the scattered light signal, and a manifestation processing unit 506 which executes a differential processing of a signal from which noise N has been removed by passing through the noise processing section 505.

The noise processing section 505 is provided with a smoothing processing unit 502 which smoothes the scattered light signal, and a filter processing unit 504 that filters the signal smoothed by the smoothing processing unit 502. In the filter processing unit 504, a set value (threshold value) obtained by calculation or actual measurement in advance is prepared. A detection value lower than the set value of the signal sent from the smoothing processing unit 502 is determined to be noise N and regarded as 0 (zero), and hence the noise N is removed. A signal S that passed through the signal converting section 507 becomes an output 500.

Incidentally, the manifestation processing unit 506 may preferably be provided because the signal S becomes liable to emerge, but it may not be provided.

Here, the noise processing by the noise processing section 505 will briefly be described.

As the factors that generate noise, they are roughly divided into two. One is externally generated noise as an unwanted signal coming inside from the outside of the device. The other one is internally generated noise as an unwanted signal generated inside the circuit, for example.

Common high-frequency disturbance noise as externally generated noise increases in terms of the proportion of noise that assumes a sharp spike form. Therefore, the smoothing processing unit 502 is provided. This smoothing processing unit 502 is capable of performing smoothing processing on the externally generated noise and thereby exerting an effect as a positive noise countermeasure. As the smoothing processing unit 502, there is mentioned ferrite core or the like as one example.

On the other hand, there are various factors for the occurrence of internally generated noise. As the typical one thereof, there is mentioned thermal noise. In general, a frequency band (range) extends to a wide band. Therefore, the filter processing unit 504 is provided. The filter processing unit 504 is capable of functioning as a band pass filter which limits the signal band from conditions for detecting internally generated noise and restrictive conditions of a sampling period and reducing noise of the band other than it, thus making it possible to increase the effect of a noise reduction by the filtering.

Of the terahertz illumination light 100, those transmitted through the electrode mixture layer 700 assume specular reflected light 670 by being reflected by the surface of the collector 710.

When the metal foreign matter 720 (metal particles) is contained in the electrode mixture layer 700 (film), a portion of the transmitted light of the terahertz illumination light 100 is reflected by the metal foreign matter 720 in the film and becomes scattered light 660, followed by entering the detection optical unit 260 placed above. The scattered light 660 is focused by a lens, a mirror or the like in the detection optical unit 260 and introduced into the scattered light detector 200.

Figure 2B:
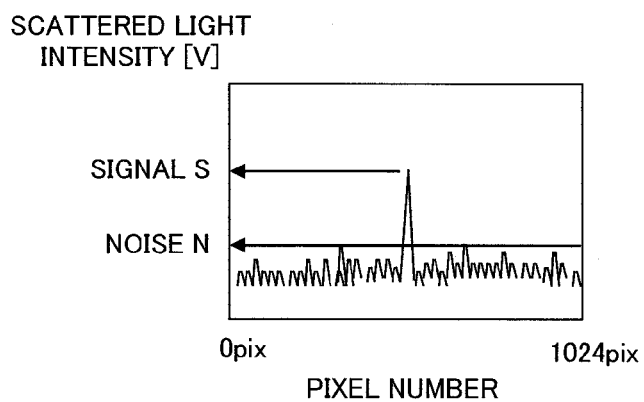
FIG. 2B is a graph showing a distribution of a scattered light of the terahertz wave.

FIG. 2B is a graph showing the distribution of the scattered light of the terahertz wave. A pixel number is taken on the horizontal axis, and the scattered light intensity is taken on the vertical axis.

In the present figure, the output of the scattered light detector 200 is one having an intensity distribution spatially and has a peak at the central part of the horizontal axis. That is, since the peak of the scattered light intensity is intended to indicate clearly that the metal foreign matter 720 has been detected, the peak of the scattered light intensity is defined as a signal S. Since the scattered light in the region of the scattered light intensity other than the peak being low is intended to be a factor that inhibits the detection of the signal S, the scattered light is referred to as noise. In the present figure, the maximum value of the noise is shown as noise N.

When expressed as the ratio between the signal S and the noise N, it is possible to easily and reliably detect metal foreign matter 720 small in particle size when a high S/N ratio is taken. That is, even when the particle size of the metal foreign matter 720 is small and the signal S is low, it is possible to determine the metal foreign matter 720 if the noise N is low.

The terahertz illumination light 100 that was not reflected by the metal foreign matter 720 is reflected by the collector 710 and assumes the specular reflected light 670, and proceeds toward a region other than the detection optical unit 260. When the specular reflected light 670 is strong, an anti-reflection part for preventing reflection may preferably be provided separately to prevent the specular reflected light 670 from becoming stray light by hitting a member such as a frame inside the device.

A transmission experiment to irradiate the active material 701 with a terahertz wave having a wavelength of about 10 times the particle size of the active material 701 was conducted and the transmittance was actually measured.

Figure 3A:
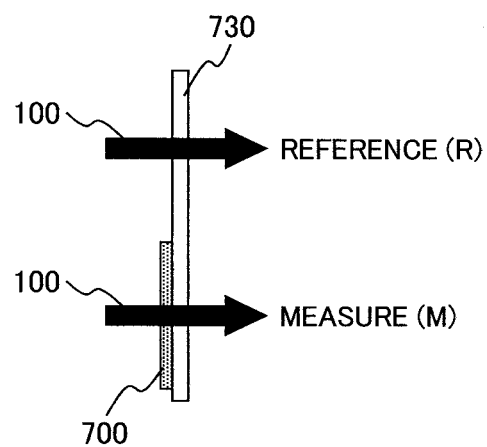
FIG. 3A is a schematic sectional view showing a sample to be subjected to measurement of transmittance.

FIG. 3A is a schematic sectional view showing a sample (sample) for measuring the transmittance.

An electrode mixture containing an active material 701 is applied to the portion of the surface of a Si wafer (silicon wafer) being a substrate 730 transmitting terahertz illumination light 100 (terahertz wave) to form an electrode mixture layer 700 of 50 μm in thickness. Thus, the base material 730 has a region formed with the electrode mixture layer 700 and a region not formed with the electrode mixture layer 700. The transmittance of the terahertz illumination light 100 in the electrode mixture layer 700 was calculated by irradiating each region with the terahertz illumination light 100 and measuring the intensity of the transmitted light.

That is, from the transmitted light intensity R in the region not formed with the electrode mixture layer 700 in the substrate 730, and the transmitted light intensity M in the region formed with the electrode mixture layer 700, M/R being the ratio of these was calculated and taken as the transmittance.

Figure 3B:
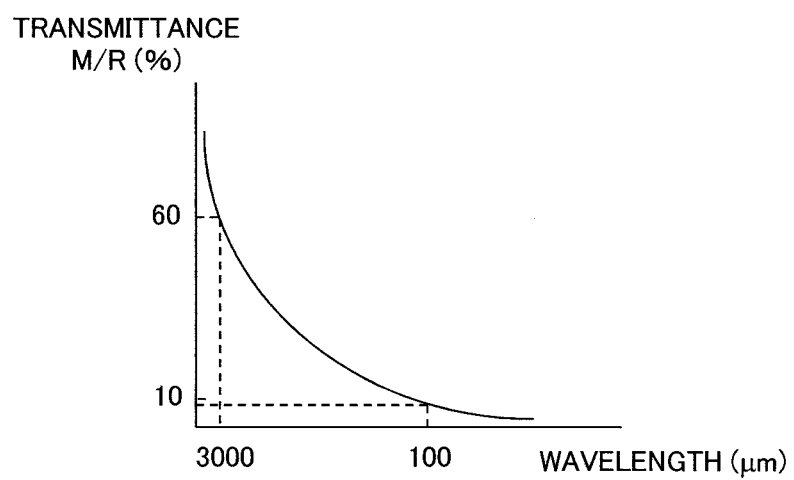
FIG. 3B is a graph showing a wavelength dependence of a transmittance of an electrode mixture layer.

FIG. 3B is a graph showing the measurement results of transmittance. The wavelength of the terahertz illumination light 100 (terahertz wave) is taken on the horizontal axis and expressed as a logarithmic axis. The transmittance M/R is taken on the vertical axis. Here, the transmittance is expressed in percentage. Further, the wavelength shown in the horizontal axis decreases in value as it proceeds in the right direction.

It is understood from the present figure that the transmittance is reduced as the wavelength of the terahertz wave becomes shorter. For example, when the wavelength is 3 mm (0.1 THz), the transmittance was 60%, whereas when the wavelength is 100 μm (3 THz), the transmittance is reduced to several percent. Thus, it is understood that the transmittance of the terahertz illumination light 100 in the electrode mixture layer 700 containing the active material 701 can be made high by appropriate selection of the wavelength.

Then, the factors that affect the intensity of the scattered light will be described.

Figure 4A:
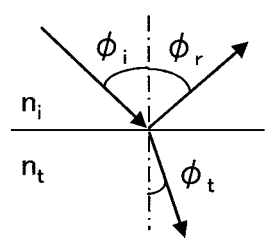
FIG. 4A is a conceptual diagram showing a state when an emitted light is reflected or transmitted at an interface.

FIG. 4A shows a state when the light emitted is reflected or transmitted at the interface.

In the present figure, it is assumed that an incident angle, a refractive angle and a reflection angle in the case where a refractive index of a medium on the side of incidence is $n_i$ and a refractive index of a medium on the side of transmission is $n_t$ are $\phi_i$, $\phi_t$ and $\phi_r$ respectively.

A scattering coefficient representing the intensity of the scattered light by the Rayleigh scattering phenomenon can be calculated by the following calculation formula (1).

$$K_s = \frac{2\pi^5}{3} n \left( \frac{m^2 - 1}{m^2 + 2} \right)^2 \frac{d^6}{\lambda^4} \quad \text{calculation formula (1)}$$

where m is reflection coefficient, n is the number of particles, d is the particle diameter, and λ is the wavelength.

A reflection coefficient m can be calculated using the following calculation formulas (2) to (4).

$$m = \sqrt{m_s^2 + m_p^2} \quad \text{calculation formula (2)}$$

$$m_s = [E_r^0 / E_i^0]_s = \frac{n_i \cos\phi_i - n_t \cos\phi_t}{n_i \cos\phi_i + n_t \cos\phi_t} \quad \text{calculation formula (3)}$$

$$m_p = [E_r^0 / E_i^0]_p = \frac{n_i \cos\phi_i - n_t \cos\phi_t}{n_i \cos\phi_i + n_t \cos\phi_t} \quad \text{calculation formula (4)}$$

where the above calculation formula (3) is intended to calculate the reflection coefficient $m_s$ of S-polarized light, and the above calculation formula (4) is intended to calculate the reflection coefficient $m_p$ of P-polarized light.

For example, according to Non-Patent Document 1, when the wavelength of light to be irradiated is 150 μm, the refractive index of aluminum is 358 and its absorption coefficient is 425. For the refractive indices and absorption coefficients of other metals such as copper, iron, SUS steel and the like as the metal foreign matter that requires other detection, sufficient data in the terahertz region is not described even in the Non-Patent Document 1. It was, however, found that they were nearly equal to those of aluminum (about three orders of magnitude) as a result inferred by extrapolating the data of the Non-Patent Document 1.

Meanwhile, the active material being a compound such as $LiCoO_2$, a conductive additive being particulates of a carbonaceous material, the binder being a resin such as polyvinylidene fluoride (PVDF), styrene butadiene rubber (SBR) or the like, etc. are contained in the electrode mixture. Even for these, sufficient data in the terahertz region is not obtained. It is, however, found that when inferred from the measurement results described in Non-Patent Document 1, the refractive index has a difference of about three orders of magnitude than the value of the metal.

Figure 4B:
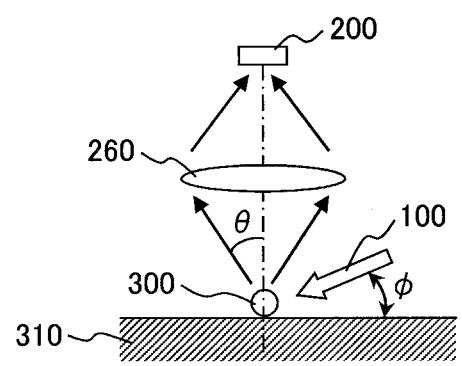
FIG. 4B is a configuration diagram showing a condition for calculating an intensity of a scattered light from a metal particle irradiated with an illumination light by a simulation.

FIG. 4B is one showing a setting condition for simulating the intensity of scattered light.

In the present figure, the terahertz illumination light 100 is applied to a substrate 310 at a predetermined illumination light elevation angle φ and scattered. The scattered light is condensed by the detection optical unit 260 having an aperture angle 2θ and converted into an electrical signal by the scattered light detector 200. The scattered light detector 200 is placed in a direction perpendicular to the substrate 310 and calculates the sum of the amount of light falling within the predetermined aperture angle $2\theta$ to determine a scattered light intensity. The substrate 310 is assumed to be made of aluminum. One foreign matter particle 300 (aluminum particle) is assumed to be put on the substrate 310. Incidentally, if the refractive index of air being the medium of the optical system is regarded as 1, the relationship between the aperture angle $2\theta$ and the numerical aperture NA is $NA=\sin\theta$.

Figure 4C:
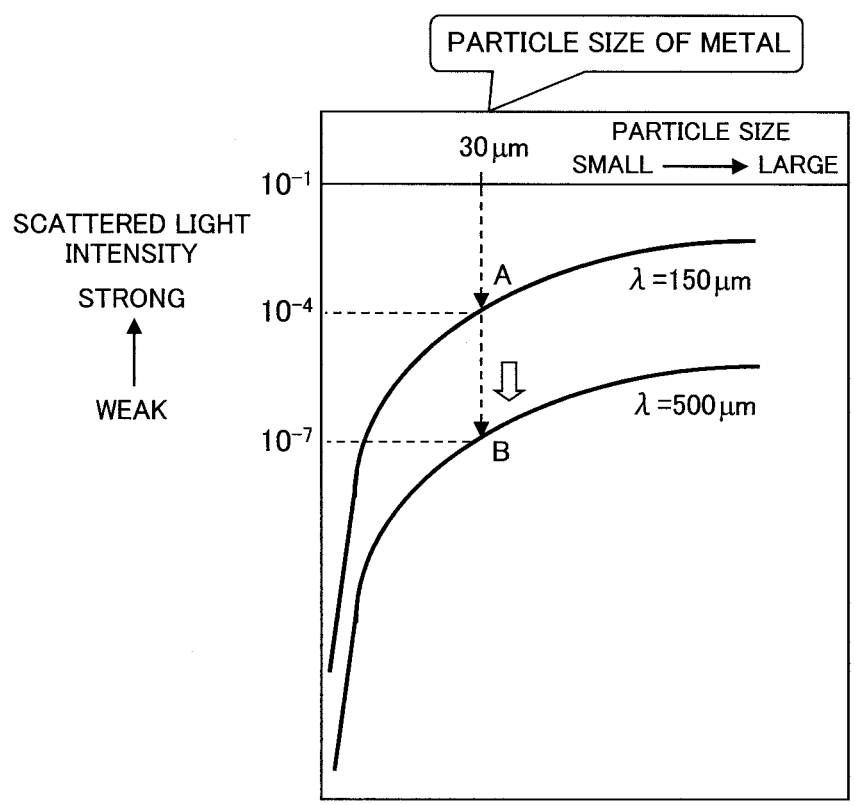
FIG. 4C is a graph showing a wavelength dependence of the intensity of the scattered light with respect to a particle size of the metal particle.

FIG. 4C shows an example of simulation results based on the setting condition of FIG. 4B. The particle size of the foreign matter particle 300 is taken on the horizontal axis, and the scattered light intensity is taken on the vertical axis and expressed as a logarithmic axis.

The present figure shows the case where the terahertz illumination light 100 (terahertz wave) is irradiated slant from ($\phi=13°$) and detected by detection optical unit 260 having an aperture angle $2\theta=40°$ (NA=0.342), which has been placed in a direction perpendicular to the substrate 310. The wavelength $\lambda$ of the terahertz illumination light 100 is shown as an example in the case of 150 μm and 500 μm.

When $\lambda=150$ μm, based on Non-Patent Document 1, the refractive index was set to 358, and the absorption coefficient was set to 425. On the other hand, when $\lambda=500$ μm, by analogy from the data in Non-Patent Document 1, the refractive index was set to 822, and the absorption coefficient was set to 869.

In the present figure, assuming that the wavelength $\lambda$ is 150 μm when the particle size of the foreign matter particle 300 (aluminum particle) placed on the substrate 310 is 30 μm, the scattered light intensity (expressed in A in the figure) becomes about $10^{-4}$ times the amount of incident light. In contrast, assuming that the wavelength $\lambda$ is 500μ when the particle size of the foreign matter particle 300 is 30 μm, the scattered light intensity (expressed in B in the figure) becomes about $10^{-7}$ times the amount of incident light. That is, the difference in signal intensity (scattered light intensity) obtained by the scattered light detector 200 results in a difference of about 1000 times. Thus, it is found that when the wavelength $\lambda$ is 500 μm, the detection of the foreign matter particle 300 is difficult in the case of weak signals, and when the wavelength $\lambda$, is 150 μm, the detection of the foreign matter particle 300 is easy.

Then, the differences in the scattered light intensity due to the reflectivity of the material will be discussed.

Figure 5:
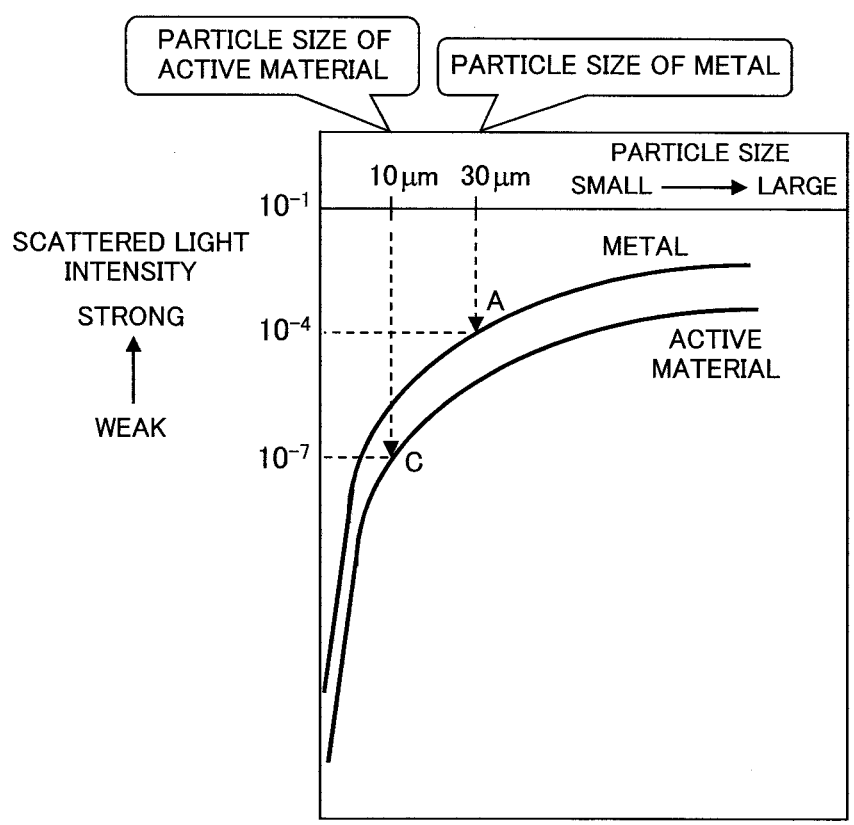
FIG. 5 is a graph showing the intensity of the scattered light which has taken into consideration the particle size and refractive index of each of an active material and the metal particles.

FIG. 5 shows the results of the execution of simulation of changes in scattered light intensity due to differences in material and particle size. A particle size is taken on the horizontal axis, and the scattered light intensity is taken on the vertical axis and expressed as a logarithmic axis.

Materials taken as targets are aluminum and an active material. The case of $\lambda=150$ μm is shown as an example.

As with FIG. 4C, the present figure also shows the case where the terahertz illumination light 100 (terahertz wave) is irradiated slat from ($\phi=13°$) and detected by the detection optical unit 260 having the aperture angle $2\theta=40°$ (NA=0.342), which has been arranged in a direction perpendicular to the substrate 310.

For aluminum, as with FIG. 4C, based on Non-Patent Document 1, the refractive index was set to 358, and the absorption coefficient was set to 425. On the other hand, for the active material, physical property values are assumed to be used assuming the $LiCoO_2$ or the like. That is, referring to data of $LiNbO_3$ or the like described in Non-Patent Document 1, it is assumed that the refractive index is 1.6, and the absorption coefficient is 0.

In the present figure, in the case of particles of aluminum 30 μm in particle size, the scattered light intensity (expressed in A in the figure) is about $10^{-4}$ times the amount of incident light. In contrast, in the case of particles of an active material 14 μm in particle size, the scattered light intensity (expressed in C in the figure) is about $10^{-7}$ times the amount of incident light. That is, it is understood that it can be detected with S/N ratio=1000.

From the above, in the detection of metal foreign matter in the active material of the LIB, the electromagnetic wave (terahertz wave) having a suitable wavelength that passes through the active material, and the difference in the scattered light intensity can be utilized. It is found that the detection of foreign matter is possible with high sensitivity.

As a result of considering the transmittance characteristics of the material and simulation results described above and further executing parameter survey, it has been found that for example, in the case of (about 60%) wavelength 3 mm (0.1 THz) high in transmittance of the active material, light to be irradiated to metal foreign matter can be increased, but the scattered light intensity is reduced to $10^{-7}$. On the other hand, it has been found that in the case of the wavelength 150 μm (2 THz) low in transmittance of the active material, the transmittance is a few percent and less reduced, but the scattered light intensity can be obtained as $10^{-4}$.

That is, since the variation in scattered light intensity is large, a terahertz wave close to a wavelength 100 μm (3 THz) is advantageous as the illumination light used to detect the scattered light. The wavelength in the range of 30 to 200 μm is suitable. On the other hand, in the case of a wavelength 500 μm, there is a high possibility that the detection of scattered light will become difficult. Therefore, the wavelength in the range of 30 μm or more and less than 500 μm is preferable.

The proper range of the wavelength of the terahertz wave is summarized as follows.

In the case of the active material and the metal foreign matter corresponding to the condition of the particle size or the like, the wavelength of the terahertz wave is preferably in the range of 30 μm or more and less than 500 μm or more preferably in the range of 30 to 200 μm. However, the desired range of wavelengths differs depending on the type of active material to be targeted, the particle size or the like, and the thickness of the electrode mixture layer.

Next, the conditions efficient to perform the scattered light detection will be discussed.

Figure 6A:
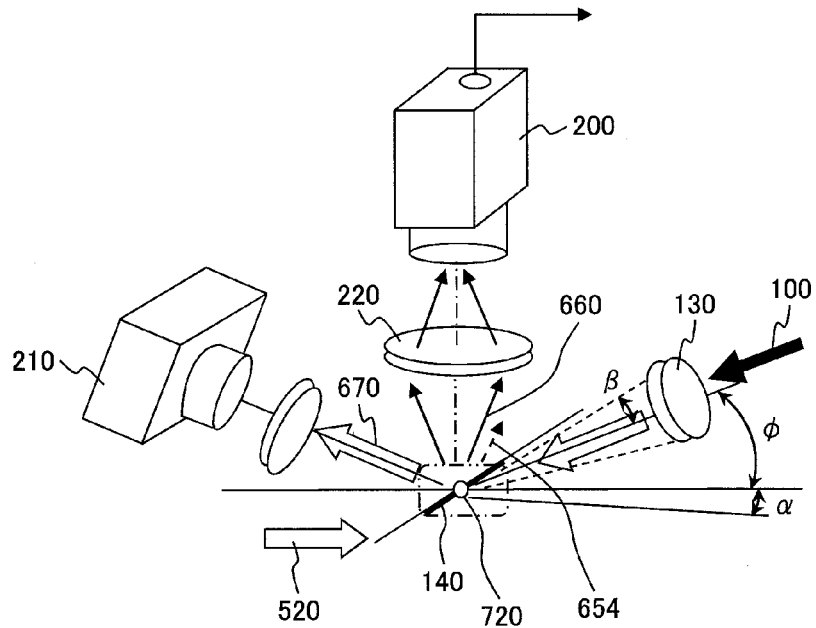
FIG. 6A is a schematic configuration diagram showing an optical system of a device for detecting foreign matter.

FIG. 6A shows a schematic configuration of an optical system of a device for detecting foreign matter.

From the demand to efficiently perform the detection of the scattered light 660, the device for detecting foreign matter shown in the present figure uses the far infrared radiation (terahertz illumination light 100).

In the present figure, the device for detecting foreign matter is composed of, as major components, an illumination light aperture 130, a scattered light detector 200 and a specular reflection light detector 210. Terahertz illumination light 100 is applied to an object (work) such as an electrode sheet or the like flowing in a work moving direction 520 to form a line-shaped light portion 140. Here, the terahertz illumination light 100 is irradiated from the direction of an illumination light azimuth angle $\alpha$ and an illumination light elevation angle $\phi$ with respect to the object. In addition, the terahertz illumination light 100 is illuminated at an illumination light aperture angle $\beta$.

The object may contain metal foreign matter 720. Many of the terahertz illumination light 100 applied to the object move toward the specular reflection light detector 210 to become specular reflected light 670. A part of the scattered light 660

(including the reflected light 654 shown in FIG. 2A) from the object moves toward the scattered light detector 200 through a scattered light detection aperture 220. A part of the reflected light from the metal foreign matter 720 is also adapted to enter the scattered light detector 200.

In the case of detecting the metal foreign matter 720 contained in the LIB electrode material as an object, by appropriately selecting the wavelength of the terahertz illumination light 100, the terahertz illumination light 100 passes through the active material and reaches the metal foreign matter 720, and the scattered light 660 reflected from the metal foreign matter 720 is also transmitted through the active material and can be detected by the scattered light detector 200. In this case, the scattered light detector 200 is preferably placed in a position where the scattered light 660 from the metal foreign matter 720 can be captured with the best sensitivity.

Further, as long as the transmittance of the active material contained in the LIB electrode material is not 100%, the reflected light 654 (shown in FIG. 2A and subsequently the same as above) is generated even from the LIB electrode material being a multi-particle structure, simultaneously with the generation of the scattered light 660 from the metal foreign matter 720. The reflected light 654 from the active material is preferably reduced from the purpose of detecting with high sensitivity, the scattered light 660 from the metal foreign matter 720.

Therefore, in the arrangement of the detection optical system of the scattered light 660, it is taken as an arrangement in which the signal of the metal foreign matter 720 is the highest and noise by the scattered light 660 from the active material is the lowest. The arrangement of the elevation angle $\phi$ of the terahertz illumination light 100, the azimuth angle $\alpha$ and the aperture angle $\beta$ of the illumination light aperture 130, and the arrangement of the scattered light detection aperture 220 and scattered light detector 200 are determined. For these arrangements, the optimum values may be determined experimentally. When the object that generates the scattered light 660, and the shape and physical property values (e.g., refractive index and absorption coefficient) of the metal foreign matter 720 are known, the optimum values of the elevation angle $\phi$ of the terahertz illumination light 100, the azimuth angle $\alpha$ and the like at which the scattered light 660 becomes strong, may be grasped using the simulation of the scattering phenomenon.

Also, although not shown in the figure, when the signal intensity ratio between the scattered light 660 and the metal foreign matter 720 changes with the P-polarized light or S-polarized light, changing the polarization direction of the terahertz illumination light 100 using a polarizing plate is also effective.

Furthermore, when the angle of the scattered light 660 and the angle of the scattered light of the metal foreign matter 720 are different, it is also possible to shield the scattered light 660 at the aperture of the detection optical detection unit and install a diaphragm in a position to pass the scattered light from the metal foreign matter 720. Further, when the detection optical unit is a Fourier transform lens, it is also possible to produce a detection optical unit for passing the scattered light from the metal foreign matter 720 by installing a stop for selectively blocking out the scattered light 660 in the Fourier transform plane.

A device for detecting foreign matter which is good in efficiency and capable of detecting the scattered light with high sensitivity can be realized in this way.

Then, the operation of the scattered light detector 200 when the inspection of the metal foreign matter 720 is conducted will be described.

Figure 6B:
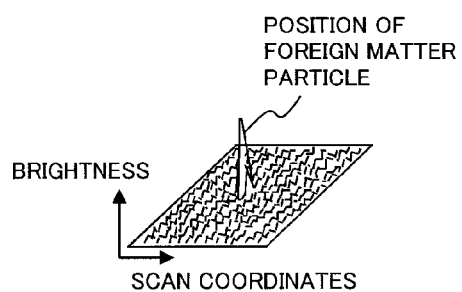
FIG. 6B is a graph showing a distribution of the scattered light measured by a scattered light detector.

FIG. 6B is a graph showing the distribution of scattered light 660 detected by the scattered light detector 200.

The present drawing is one showing in three-dimensional coordinates, the distribution of brightness (incident light intensity) of the scattered light 660 two-dimensionally incident on the sensor of the scattered light detector 200.

To efficiently inspect a large area in a short time, the conditions shown below are necessary.

First, rather than a single sensor, the scattered light detector 200 preferably has sensors (referred to as two-dimensional sensors) arranged two-dimensionally or sensors (referred to as one-dimensional sensors) arranged one-dimensionally.

Further, the terahertz illumination light 100 is applied in a large area onto the surface of the object and applied to the surface of the object as a line-shaped light portion 140 to be a conjugate with a two-dimensional sensor or a one-dimensional sensor. In the case of the one-dimensional sensors, an illumination optical system including the illumination light aperture 130 is arranged to form the line-shaped light portion 140 in parallel to the direction in which the one-dimensional sensors are arranged. In the case of the two-dimensional sensors, an illumination optical system for forming a bright portion wide in planar form is desirable.

The illumination optical system generates a desired shape by using a member including a condensing lens, a reflecting mirror or the like and forms a light portion uniform in illumination intensity so as to reduce the quantity difference between the central part thereof and its peripheral portion. By repeating the measurement while moving an object for inspection (work) in a direction (work moving direction 520) perpendicular to the length direction of the line-shaped light portion 140, a large area can be inspected under the same conditions.

The size of the inspection area and the size of the terahertz illumination light 100 are determined considering the size of a detection pixel required, the number of pixels of the scattered light detector 200, resolution, cost-effectiveness, etc. Then, further when it is necessary to perform simultaneous inspection in a wide range, preferably, diction optical systems each comprised of the illumination light aperture 130, the scattered light detector 200, the specular reflection light detector 210 and the like may be installed in parallel in plural form.

To perform the detection of foreign matter by the scattered light 660 with high sensitivity, there is a need to efficiently detect the scattered light 660 of the metal foreign matter 720 (metal particles) contained in the object by the scattered light detector 200. As the conditions in this case, the relationship between the sensor side of the scattered light detector 200 and the object side being aligned with the so-called focus is required. In order to create this condition, it is necessary to inspect the object side in an always focus-aligned constant state. To this end, it is desirable to realize the function of auto-focus. The auto-focus is a function that automatically adjusts the focal length, and is made by the focal distance adjusting unit.

An example of realizing the auto-focus by using the specular reflected light 670 will next be described using FIGS. 6A and 6C.

Figure 6C:
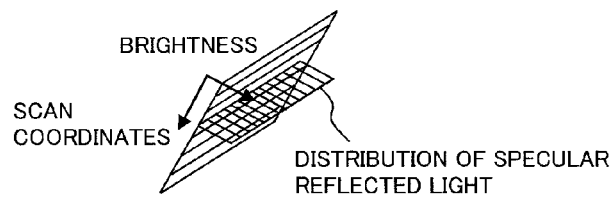
FIG. 6C is a graph showing a distribution of a specular reflected light measured by a specular reflection light detector.

FIG. 6C is a graph showing the distribution of the specular reflected light 670 detected by the specular reflection light detector 210.

The present drawing is one showing in three-dimensional coordinates, the distribution of brightness (incident light intensity) of the specular reflected light 670 two-dimensionally incident on the sensor of the specular reflection light detector 210.

In order to detect the specular reflected light 670, the specular reflection light detector 210 having a two-dimensional sensor or a one-dimensional sensor (called simply sensor) is placed in the position conjugate to the object point in the optical path of the specular reflected light 670. When the position where the terahertz illumination light 100 is reflected, i.e. the position (corresponding to the position of the object point in the detection of the scattered light 660) is moved up and down, the distribution of the specular reflected light 670 in the sensor varies depending on its moving distance. This means that the distribution of the specular reflected light 670 in the sensor corresponds to the position of the terahertz illumination light 100. The distribution of the regularly reflected light 670 detected in the sensor is fed back to control the position of the position of the object point. Thus, it is possible to realize the function of autofocus.

There are a heterodyne method and a lock-in detection method as approaches of manifestation to realize the scattered light detection with higher sensitivity. The method will be described using FIG. 7.

Figure 7:
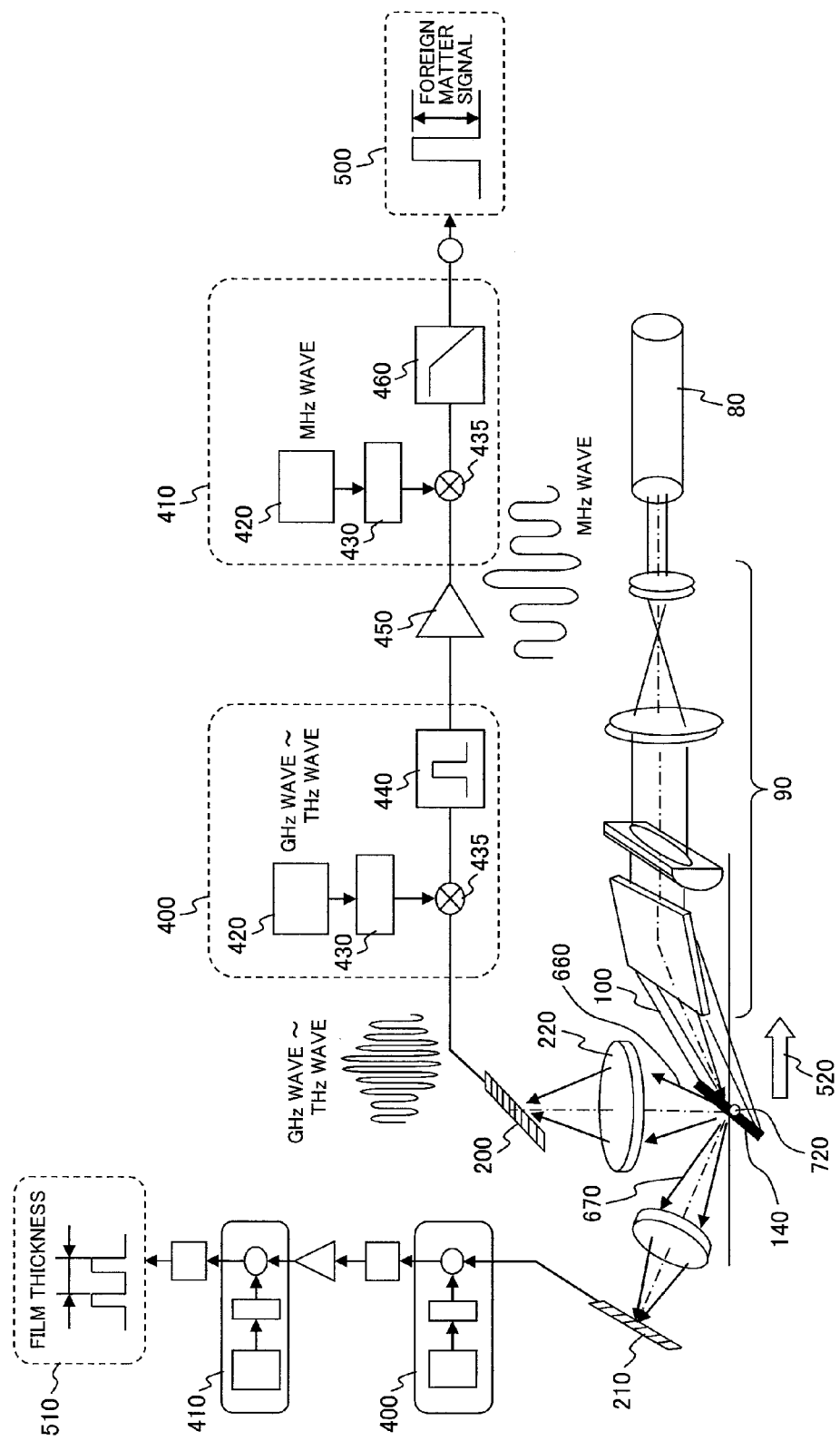
FIG. 7 is a configuration diagram showing a circuit for improving a sensitivity of a foreign matter inspecting apparatus.

FIG. 7 is one showing a circuit configuration for improving the sensitivity of a foreign matter inspecting apparatus.

In the present figure, there is shown a circuit configuration for processing by heterodyne 400 and a lock-in amplifier 410, a signal detected by a specular reflection light detector 210 and a scattered light detector 200. The heterodyne 400 and the lock-in amplifier 410 respectively include a local oscillator 420 (Local Oscillator), an attenuator 430 (ATT) and an integration circuit 435.

Terahertz illumination light 100 is irradiated from a light source 80 and applied through an illumination optical system 90 to form a line-shaped light portion 140.

When the amount of scattered light 660 from metal foreign matter 720 is reduced and thereby a signal voltage value decreases, and it becomes close to noise due to the scattered light 660 from an active material or a voltage value of noise generated from a detection circuit, the detection of the metal foreign matter cannot be performed stably. Therefore, it is necessary to take measures against a noise reduction separately. As a means for reducing the noise, the heterodyne detection method and the lock-in detection method are desirable.

First, the heterodyne detection method as a manifestation processing unit will be described.

When the metal foreign matter 720 is detected, the amount of the scattered light 660 is also reduced as the size of the metal foreign matter 720 becomes smaller. The noise is also amplified when a signal is amplified by an amplifier for stable detection, thus resulting in erroneous detection. Therefore, in order to reduce the amplifier noise during amplification, a signal of a frequency comparable to the signal of the scattered light detected by the scattered light detector 200 is supplied to the integration circuit 435 by the local oscillator 420 and the attenuator 430. Thus, the frequency of the detection signal is converted (reduced) to a MHz band, and signal amplification in the region of amplifier reduction noise is performed. In this case, the heterodyne 400 is used as a means for converting the frequency of the detection signal. For example, when a signal of a frequency in a THz+MHz band is put to a detection signal of a terahertz region as a reference signal at the detector, it is possible to perform conversion to a MHz band of a difference frequency of the detection signal.

It is possible to eliminate noise by a MHz-band band-pass filter 440 (BPF) and obtain a noise-reduced MHz-band output by putting a low noise amplifier 450 in its subsequent stage.

When this relationship is expressed in a numerical formula, measurement light, reference light and interference light are respectively represented by the following calculation formulas (5), (6) and (7).

$$I_1 = A_1 \exp(\omega_1 t + \phi_1) \qquad \text{calculation formula (5)}$$

$$I_2 = A_2 \exp(\omega_2 t + \phi_2) \qquad \text{calculation formula (6)}$$

$$I = A_1^2 + A_2^2 + 2A_1 A_2 \cos[(\omega_1 - \omega_2)t + (\phi_1 - \phi_2)] \qquad \text{calculation formula (7)}$$

where $\omega_1$ is the frequency of the terahertz illumination light 100 (measurement light beam), $\omega_2$ is the frequency integrated at the heterodyne 400, and $\omega_1 - \omega_2$ is the target value of the frequency of MHz output from the heterodyne. The frequency of $\omega_2$ is selected in such a manner that $\omega_1 - \omega_2$ reaches a few MHz.

Then, likewise, a method using the lock-in amplifier 410 as a means to reduce the noise from the detection signal will be described.

As shown in FIG. 7, there is a lock-in detection method as a means for manifesting and taking out a foreign matter detection signal with noise being reduced by the heterodyne 400. In this lock-in detection method, a signal of a frequency in a MHz band, which is comparable to the signal detected by the heterodyne 400, is supplied from the local oscillator 420 to the integration circuit 435 via the attenuator 430.

A change in the signal in this case is represented by the following calculation formula (8) as an expression of the intensity of a composite wave.

$$\begin{aligned} I(\omega) &= A \sin\omega t \cdot \sin\omega \qquad \text{calculation formula (8)} \\ &= \frac{A}{2}[\cos(0) + \cos 2\omega t] \\ &= \frac{A}{2}\cos(0) \\ &= \frac{A}{2} \end{aligned}$$

A $2\omega$ component is blocked by via a low-pass filter 460 (LPF) disposed in the subsequent stage. A signal obtained as an output by this signal processing is a scattered light signal 500 of the metal foreign matter 720 and becomes A/2 shown in the above calculation formula (8).

By performing the detection signal processing described above, it is possible to reduce noise and detect with high sensitivity, the scattered light signal 500 from the metal foreign matter 720 small in size, thus making it possible to achieve high sensitization of the detection capability.

Incidentally, in addition to the detection means of the small signal such as the above heterodyne detection method or the like, a similar noise reduction effect can be brought about even by a method having a synchronous detecting unit and a lock-in amplifier and utilizing synchronous detection and a lock-in amplifier, using these. This method is a time-proven method as for transmission and reception of a general AM radio. More specifically, it is one in which a modulation frequency is added to the transmission side to apply modulation, followed by being transmitted to space, and reception is possible by selecting only the same frequency as the transmission side on the reception side. The selection of the frequency on the reception side makes it possible to eliminate noise and thereafter detect with high sensitivity, only a foreign matter signal from the lock-in amplifier.

The description of the foreign matter inspection described above relates to the fact that the terahertz wave is transmitted through the electrode film of the LIB, the metal foreign matter therein can be detected, but the similar phenomenon and effect are established even in the case of other substances. For example, it can be applied even to foreign matter detection in the dielectric material such as ceramics, a resin member or the like, which is the multi-particle structure formed by solidifying the particles.

Further, in the detection of the foreign matter in the electrode film of the LIB, the effect is described with the metal foreign matter as a target, but particles of foreign matter can be detected due to the occurrence of a difference in the amount of scattered light where there is a refractive index difference (difference in dielectric constant) between the above and a dielectric constituting a film, even if being not a metal.

Then, a method of detecting the film thickness of the electrode mixture layer containing the active material and the depth of the metal foreign matter will be described.

Figure 8A:
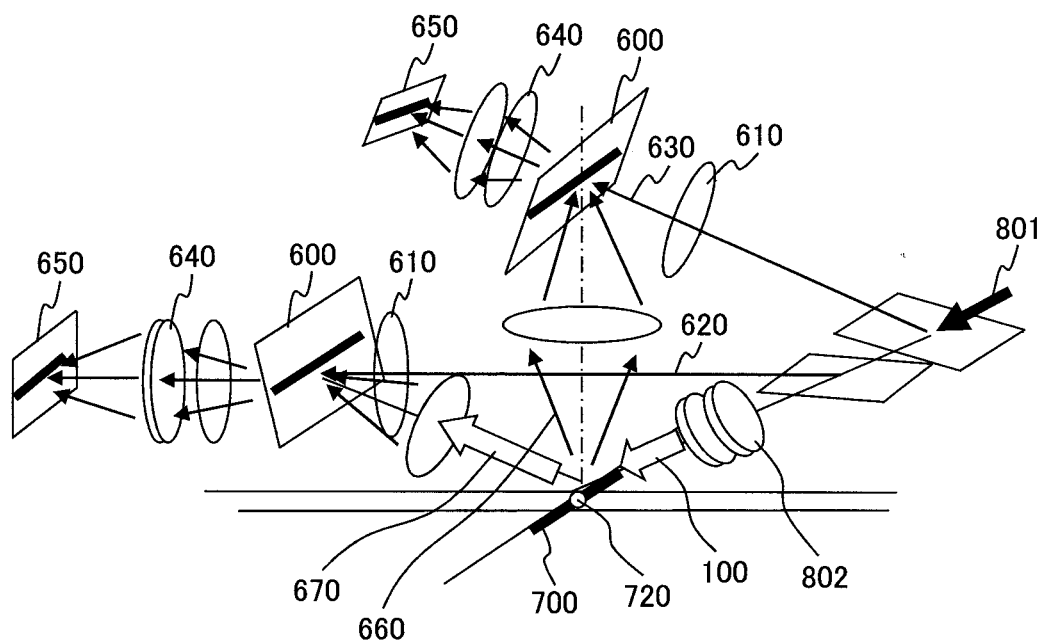
FIG. 8A is a schematic configuration diagram showing an optical system for speeding up a detection by the foreign matter inspecting apparatus.

FIG. 8A is one which shows a configuration in which an optical system is devised to perform detection in the region of near-infrared or visible light. This is one adapted to speed up the detection and applicable to the mass production line of an object such as an electrode sheet.

In the present figure, there is shown an example of detecting specular reflected light 670 by a two-dimensional planar photoelectric conversion element (light-receiving sensor) or a one-dimensional photoelectric conversion element (line sensor). The planar photoelectric conversion element is a kind of two-dimensional sensor, and the one-dimensional photoelectric conversion element is a kind of one-dimensional sensor.

First, an example of the speeding-up of detection will be described.

In addition to a bolometer type detection method for thermally converting a terahertz wave used to detect scattered light 660 to thereby detect the same, there is a detection method of performing conversion to visible light using a non-linear crystal device (EO crystal device 600) to provide photoelectric conversion.

In the case of each sensor that applies a bolometer thereto, a response time of a few msec (milliseconds) is required, and its operation speed is the limit of high-speed reading. In contrast, in the method of performing detection using the EO crystal device 600 (electro-optical crystal device), it is possible to shorten the wavelength region of sensing. For example, it can be in the region of visible light to infrared light. Therefore, it is possible to utilize a quantum type detector capable of fast response and fast the operating speed. That is, it is possible to obtain a response of μsec (microseconds).

Thus, it is possible to detect, in real time with satisfactory accuracy, a change in the thickness of the electrode mixture layer 700 containing the metal foreign matter 720, and a change in the position of autofocus.

The EO crystal device 600 is intended to utilize the Pockels effect.

The Pockels effect is a phenomenon in which when an electric field E is applied to the crystal device, the refractive index in a certain crystal direction varies due to the electric field E.

In the present figure, the terahertz illumination light 100 (terahertz wave) is irradiated to the electrode mixture layer 700 including the metal foreign matter 720 so that specular reflected light 670 is generated. Also, a part of the nanosecond pulsed laser (whose wavelength is a region of infrared light or visible light) before generating the terahertz illumination light 100 (terahertz wave) by a non-linear crystal is branched as the probe light 620. The probe light 620 is made incident into the EO crystal device 600 placed in the specular reflection light detection optical system via the polarizing plate 610, thereby causing the Pockels effect using the electric field energy of the terahertz illumination light 100 and varying the refractive index of the EO crystal device 600. That is, when laser light is irradiated as the probe light 620, the optical length at the time that the probe light 620 passes through the EO crystal device 600 varies. Thus, the phase of the probe light 620 having passed therethrough changes. Due to the change in the phase, the polarization direction of the probe light 620 incident therein changes. By installing the polarizing plate 610 on the inlet side of the EO crystal device 600 and the detection light plate 640 on the outlet side thereof respectively in such a manner that they are at a proper angle to the polarization angle of the probe light 620, the change in phase becomes a change in polarization angle and can be detected as a change in received light quantity.

By detecting the fluctuations in the passing light quantity by the quantum type infrared and visible light detector 650, variations in light quantity of the terahertz wave are detected. That is, it is possible to detect, at high speed, variations in the reflection position of the terahertz illumination light 100, the film thickness and the like.

Further, an example using the EO crystal device 600 in the scattered light detection optical system will be described.

In regard to the use of the principle of the Pockels effect, it is similar as in the case of using the EO crystal device 600 in the specular reflection light detection optical system. However, when the scattered light 660 is generated, pump light is incident on the EO crystal device 600. The refractive index of the EO crystal device 600 varies due to the scattered light 660. At this time, when laser light is irradiated as the probe light 630, the optical path length at the time that it passes through the EO crystal device 600 varies. Here, the probe light 630 used in the scattered light detection optical system is one obtained by branching nanosecond pulsed laser (whose wavelength is in the region of infrared light or visible light) before generating terahertz illumination light 100 with a non-linear crystal and causing the same to pass through the polarizing plate 610 to perform its conversion.

Thus, the phase of the probe light 630 having passed therethrough changes. The polarization direction of the incident probe light 630 changes with the change in the phase. By installing the polarizing plate 610 on the inlet side of the EO crystal device and the detection light plate 640 on the outlet side thereof respectively in such a manner that they are at a proper angle to the polarization angle of the probe light 630, the scattered light 660 of the metal foreign matter 720 can be detected at high speed and with high sensitivity using the difference in the polarization direction of the probe light 630.

The system shown in the present figure is a method for extracting the Pockels effect of the EO crystal device 600 based on the terahertz wave by the phase change of the passing laser light. The change in the phase of the laser light is however generated even by the reflection of the EO crystal device 600. Although not shown in the figure, the detection of the terahertz wave is made possible by irradiating laser light from the sensor side and detecting the reflected light from the EO crystal device 600 by the sensor similarly to the transmitted light with the change in the phase by the polarizing plate 610 as a change in light quantity. By arranging the reflection type EO crystal devices 600 in parallel, it is possible to simultaneously inspect large areas.

Figure 8B:
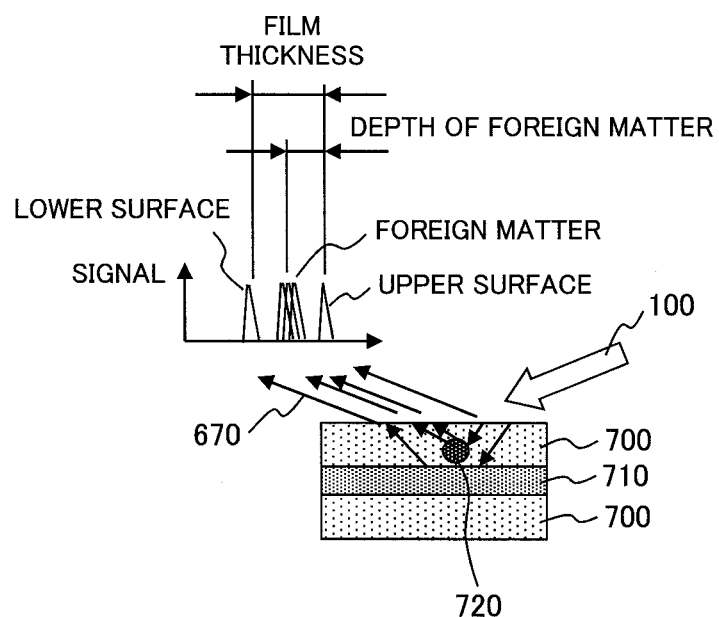
FIG. 8B is an explanatory view showing a relationship between the intensity of the specular reflected light and a film thickness and a depth of a foreign matter.
Figure 8C:
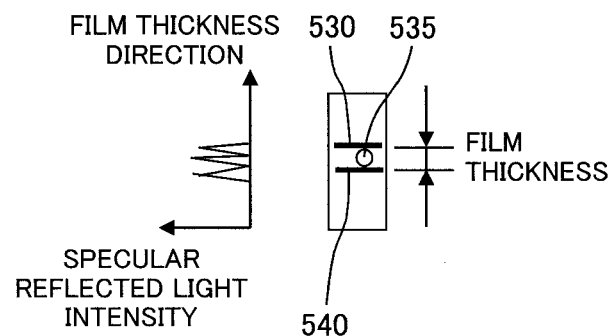
FIG. 8C is a typical diagram showing a method of calculating the film thickness from the distribution of the intensity of the specular reflected light.

FIG. 8B is an explanatory diagram showing the relationship between the film thickness of the specular reflected light intensity and the depth of the foreign matter. FIG. 8C is a typical diagram showing a method of calculating the film thickness from the distribution of the specular reflected light intensity.

As shown in FIG. 8B, the specular reflected light 670 from the electrode mixture layer 700 includes specular reflected light (upper surface reflected light 530 of FIG. 8C) from the upper surface of the electrode mixture layer 700 and specular reflected light (lower surface reflected light 540 of FIG. 8C) from the lower surface of the electrode mixture layer 700.

By adjusting the magnification of the detection optical unit of the specular reflected light 670, it is possible to recognize as position information, the upper and lower surfaces of the electrode mixture layer 700 at the infrared and visible light detector 650. Further, by detecting the distance between the lower surface and the upper surface, it is possible to detect the film thickness (thickness) of the electrode mixture layer 700.

In the lithium ion secondary battery, the thickness of the electrode mixture layer 700 affects the battery performance. Conventionally, the thickness of the electrode mixture layer 700 is measured using other means and set as a management item in the process of production.

An effect is high in that the thickness of the electrode mixture layer 700 can simultaneously be detected in the process of the foreign matter inspection using the scattered light 660 using the method shown in each of FIG. 8A to 8C against such a background.

In the inspection of the film thickness by the specular reflected light 670, when the metal foreign matter 720 is contained in the electrode mixture layer 700, each reflected signal (foreign matter reflected light 535 of FIG. 8C) from the metal foreign matter 720 can be detected in the information of the film thickness. In this case, as shown in FIG. 8B, information about the depth in which the metal foreign matter 720 is buried can be detected simultaneously.

Then, an example of applying a component analysis by a terahertz wave to inspecting the LIB will be described.

Figure 9A:
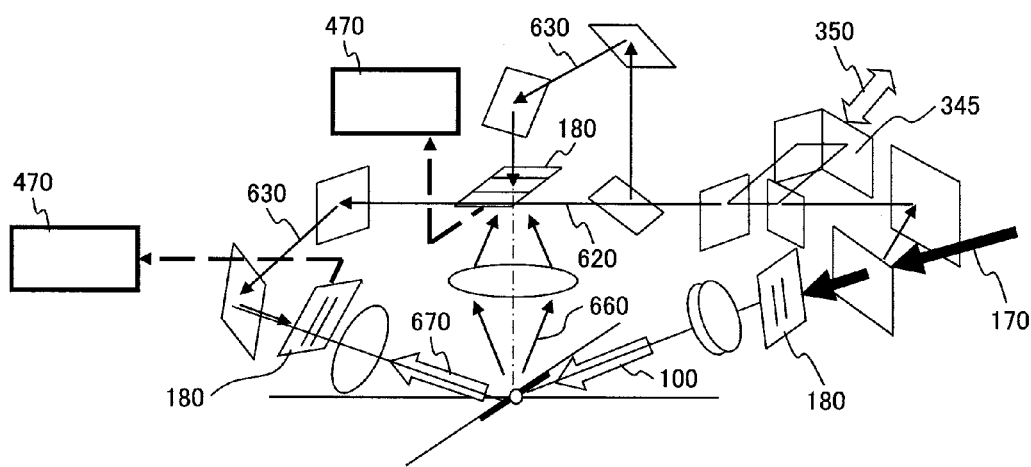
FIG. 9A is a schematic configuration diagram showing a foreign matter inspecting apparatus having a moisture analysis function and a foreign matter component analysis function.
Figure 9B:
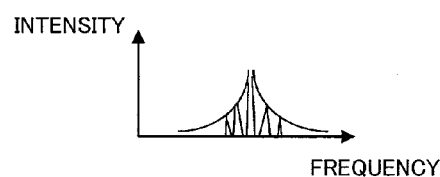
FIG. 9B is a graph showing a frequency distribution of an illumination light.
Figure 9C:
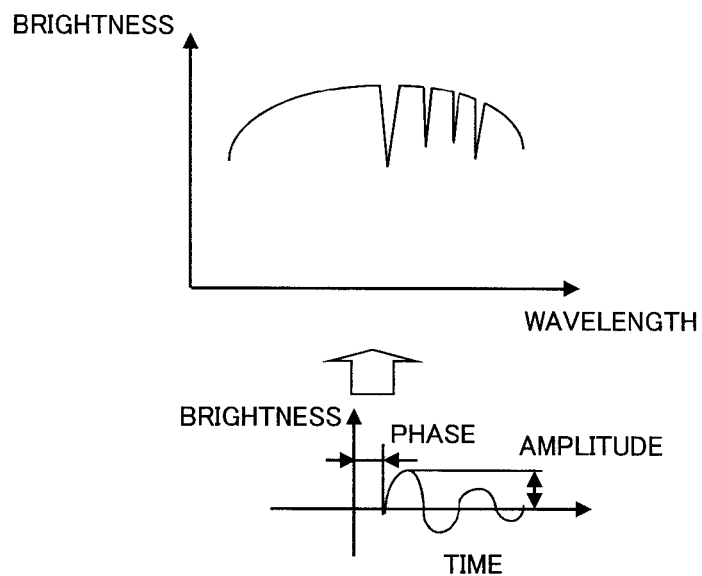
FIG. 9C is a graph showing a spectrum of the foreign matter.
Figure 9D:
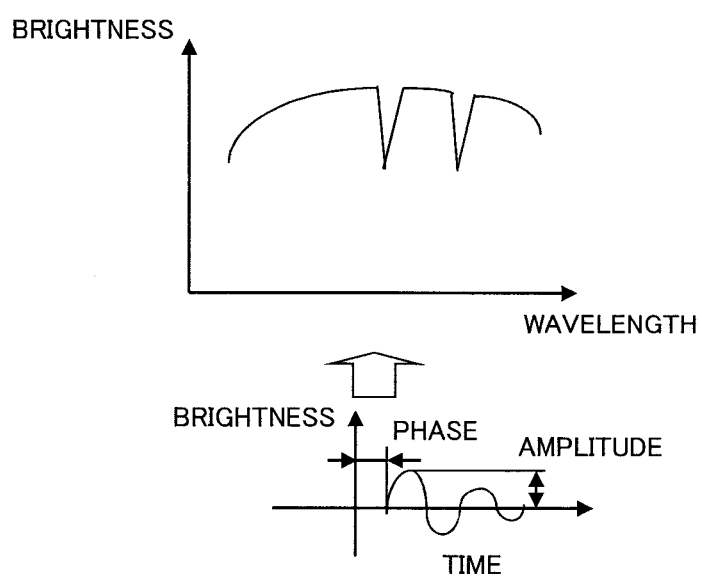
FIG. 9D is a graph showing a spectrum of the moisture.

FIG. 9A is a schematic configuration diagram showing a foreign matter inspecting apparatus having a moisture analysis function and a foreign matter component analysis function. FIG. 9B is a graph showing the frequency distribution of illumination light. FIG. 9C is a graph showing the spectrum of moisture. FIG. 9D is a graph showing the spectrum of foreign matter.

Since the terahertz wave is the light (electromagnetic wave) whose wavelength is several tens µm to several hundred micrometers, the terahertz wave causes vibration and absorption phenomena at the molecular level in the material irradiated. In the method of irradiating material (object) targeted for analysis with pulsed terahertz illumination light 100 (terahertz wave) and detecting the phase and waveform of the reflected wave in synchronization with a pulse of femtosecond pulsed laser 170, it is possible to measure the intensity of light quantity of the terahertz wave by spectrum.

From this data, it is possible to obtain a characteristic graph by spectrum with a change in the spectrum taken as the horizontal axis and the intensity of light taken as the vertical axis. Recently, the research on the use of terahertz waves has progressed, and the variation in the spectrum has been found to exhibit a characteristic distribution depending on the components of molecules. In the field of analysis, the distribution characteristic by the spectrum is called a fingerprint of a material.

In FIG. 9A, the femtosecond pulsed laser 170 is converted into the terahertz illumination light 100 by a photoconductive antenna element 180 (photoconductive antenna InGa electrostrictive element), which is irradiated to the object. Some of the femtosecond pulsed laser 170 is branched and used as probe light 630 via a reflecting plate 345 or the like. The reflecting plate 345 is movable in a reflecting plate moving direction 350. Thus, it is possible to adjust the optical path length of the probe light 630. In the present figure, the probe light 630 is applied to the photoconductive antenna element 180 that detects scattered light 660 and specular reflected light 670. Further, the probe light 630 is incident from the back side of the surface of the photoconductive antenna element 180 on which the scattered light 660 and the specular reflected light 670 are incident. A signal output 470 is obtained from the photoconductive antenna element 180 that detects the scattered light 660 and the specular reflected light 670.

As shown in FIG. 9B, the femtosecond pulsed laser 170 has a broad frequency distribution.

Then, an analysis example (FIGS. 9C and 9D) of moisture and foreign matter will be explained.

By branching the specular reflected light 670 by a detection optical system, it is possible to simultaneously realize an auto-focus function and the analysis of moisture contained in the LIB. Furthermore, it is also possible to analyze the components of the foreign matter detected from the scattered light in a similar system.

In the following description, only matters related to the analysis will be described.

The analysis of the moisture is carried out using the signal output 470 obtained from the photoconductive antenna element 180 that is a specular reflection light detector.

The femtosecond pulsed laser 170 is used as a light source to generate a broadband terahertz wave using the photoconductive antenna element 180. By irradiating the electrode sheet of the LIB with the broadband terahertz wave and converting its specular reflected light into an electrical signal by the photoconductive antenna element 180, it is possible to obtain information of the phase of the reflected light and the amplitude of each wavelength. Since the spectrum of the reflected light is a region from a sub THz to a few THz, it becomes a region that can detect spectra of the molecules of moisture exactly.

By utilizing this, it is possible to detect a spectral distribution specific to the moisture molecules and hence verify the presence of moisture.

FIG. 9C is one showing typically the fingerprint spectrum of moisture measured in the terahertz wave.

The fingerprint spectrum of moisture is obtained by converting the phase and amplitude of the brightness of specular reflected light.

When the moisture is contained in the active material in the LIB when the LIB operates as a battery, the movement of Li ions is inhibited. Therefore, in the normal production line, the moisture is prevented from adhering to a dry room, and focus is put on drying of the active material. Performing inspection of the moisture content at the same time as the foreign matter inspection as one function of the foreign matter inspecting apparatus leads to a major functional improvement as an inspecting device.

A description will be made below of the case where the analysis function is added to the scattered light detection optical system.

As typically shown in FIG. 9D, the spectra of the components of the electrode mixture layer and the foreign matter contained in the electrode mixture layer are detected from the components of the scattered light. Therefore, when the foreign matter is not a metal, it is possible to analyze the spectral content of foreign matter in the film by analysis of the wavelength of the scattered light. This is intended to utilize a phenomenon that a change appears in the reflection spectrum of the scattered light from the vibration at the molecular level. The spectrum of the foreign matter is obtained by converting the phase and amplitude of the brightness of the scattered light from the foreign matter. When the management of the process is performed, it is possible to, if the components of the foreign matter are known, seize the factor of occurrence of the foreign matter and quickly perform a reduction in the foreign matter, thus bringing about a large effect.

The functions described above have been separately described for clarity. Since, however, these detection functions are independent respectively, the respective functions can also be realized simultaneously by using light splitting means such as a beam splitter or a prism in the specular reflection optical system or scattering optical system.

In the example of the analysis shown in FIG. 9A, the femtosecond pulsed laser 170 is used. In the case of the foreign matter inspection carried out by detecting the scattered light, the energy of the terahertz wave is desirable. Therefore, as shown in FIG. 9A, the detection of the scattered light is realizable even by using the femtosecond pulsed laser 170 as a light source and converting the femtosecond pulsed laser 170 to obtain terahertz illumination light 100. The analysis and scattered light detection can be realized simultaneously.

Figure 10A:
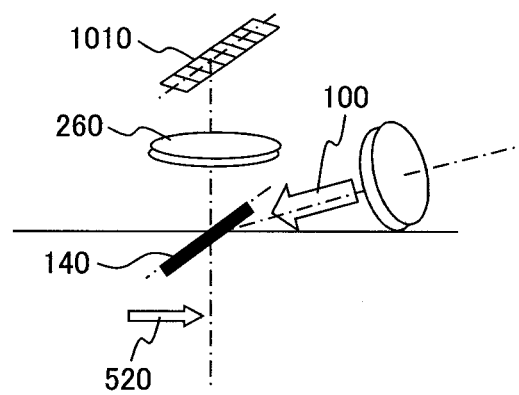
FIG. 10A is a schematic configuration diagram showing a foreign matter inspecting apparatus which performs the detection of the scattered light by a one-dimensional sensor.
Figure 10B:
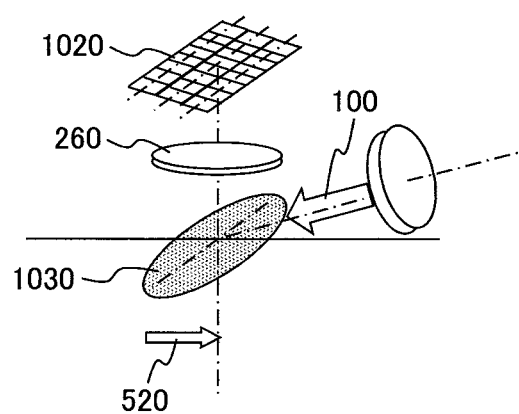
FIG. 10B is a schematic configuration diagram showing a foreign matter inspecting apparatus which performs the detection of scattered light by a two-dimensional sensor.

FIG. 10A is a typical diagram showing a configuration where the detection of scattered light is performed by the one-dimensional sensor. FIG. 10B is a typical diagram showing a configuration where the detection of scattered light is performed by the two-dimensional sensor. Here, the one-dimensional sensor is one in which a plurality of sensors are arranged in a row. The two-dimensional sensor is one in which a plurality of sensors are arranged in plural rows.

In FIG. 10A, terahertz illumination light 100 is applied to a work moved in a work moving direction 520 to assume line-shaped illumination 140. The scattered light from here is detected by the one-dimensional sensor 1010 via the detection optical unit 260. The one-dimensional sensor 1010 is preferably disposed in a direction orthogonal to the work moving direction 520.

In FIG. 10B, terahertz illumination light 100 is applied to a work moved in the work moving direction 520 to assume planar illumination 1030. The scattered light from here is detected by the two-dimensional sensor 1020 via the detection optical unit 260.

The features of the one-dimensional sensor and two-dimensional sensor will be described below.

The one-dimensional sensor is generally inexpensive. Further, since the time required to read the detected signal is short, the measurement of each image can be performed at high speed. Further, a wide object can be inspected at high speed by using the number of pixels in one row corresponding to a few thousands of pixels.

Incidentally, moving the work is desirable for the one-dimensional sensor upon examining the surface of the planar member.

The two-dimensional sensor is able to obtain information on a large area by one collection of data. Further, it is possible to easily manifest defects from wide area information.

Incidentally, it is desirable that the two-dimensional sensor uses illumination light illuminating a large area in order to maximize its data collection function. Further, since the two-dimensional sensor has more image information is large than the one-dimensional sensor, the two-dimensional sensor is preferably provided with a buffer memory and a calculation unit having a parallel processing function in order to perform an image measurement at high speed. The above calculation unit is desirable also for smoothing the movement of the work.

Figure 11:
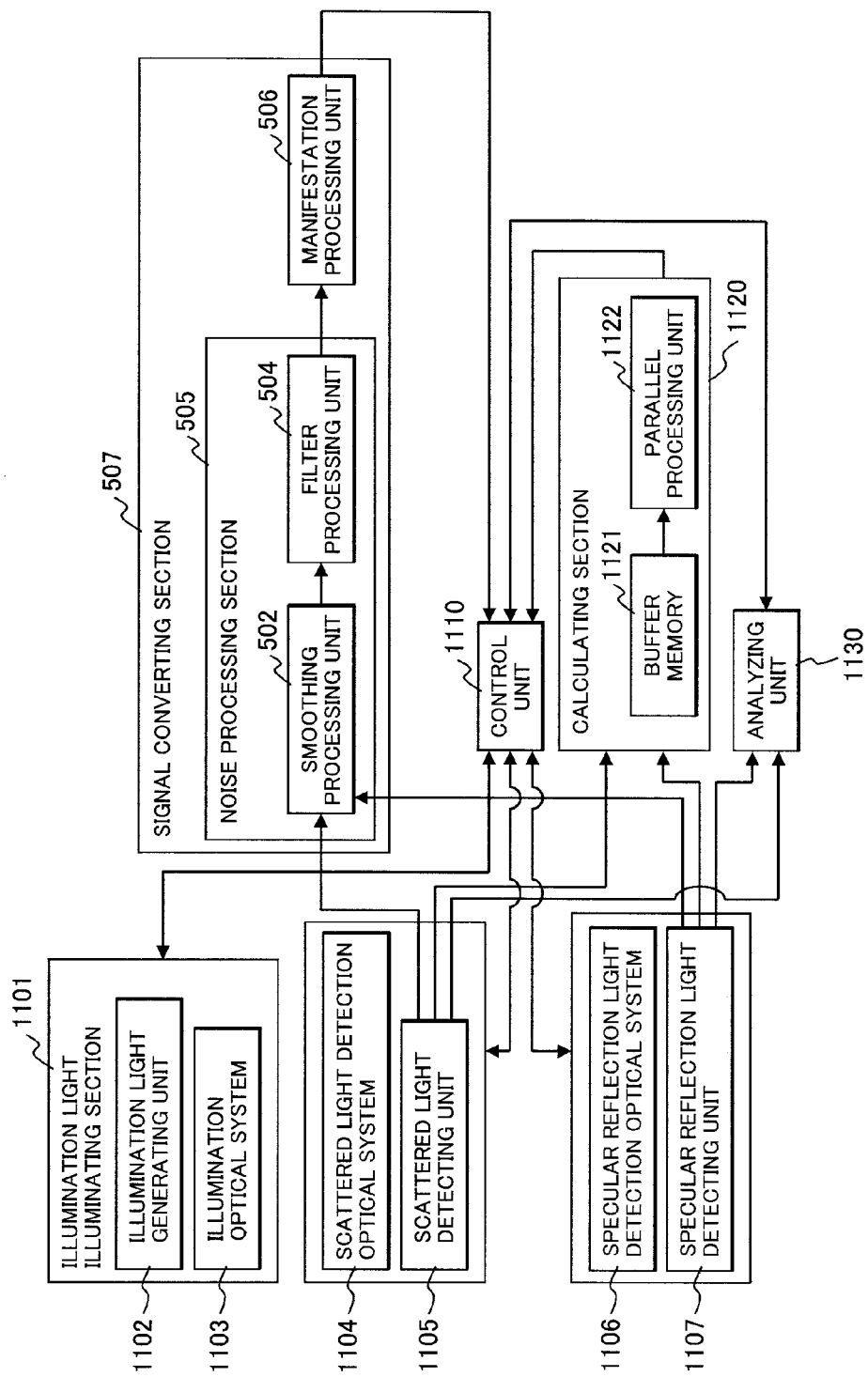
FIG. 11 is a block diagram showing a circuit configuration of the foreign matter inspecting apparatus.

FIG. 11 is one in which an example of a circuit configuration of a foreign matter inspecting apparatus is summarized as a block diagram.

In the present figure, illumination light is irradiated toward an object from an illumination light illuminating unit 1101 including an illumination light generating unit 1102 and an illumination optical system 1103. Scattered light from the object is received by a scattered light detecting unit 1105 through a scattered light detection optical system 1104. Further, specular reflected light from the object is received by a specular reflection light detecting unit 1107 via a specular reflection light detection optical system 1106. These are controlled in operation by a control unit 1110.

A signal obtained by each of the scattered light detecting unit 1105 and the specular reflection light detecting unit 1107 is transmitted to the smoothing processing unit 502 of the signal converting section 507 and transmitted to the control unit 1110 via the filter processing unit 504 and the manifestation processing unit 506. Here, the smoothing processing unit 502 and the filter processing unit 504 constitute a noise processing section 505.

When the signal becomes enormous and it becomes difficult to process the signals in real time such as the case where the scattered light detecting unit 1105 and the specular reflection light detecting unit 1107 are provided with a two-dimensional sensor, etc., the signals obtained by the scattered light detecting unit 1105 and the specular reflection light detecting unit 1107 are transmitted to the calculating section 1120 and transmitted to the control unit 1110 via a buffer memory 1121 and a parallel processing unit 1122. Thus, it is possible to prevent the overflow of each signal in the control unit 1110.

The signals obtained by the scattered light detecting section 1105 and the specular reflection light detecting unit 1107 are set to the analyzing unit 1130, where the presence or absence of moisture, the type of foreign matter, etc. can be analyzed.

The effects of the present invention will collectively be explained below.

In the case of detecting a conductive material (metal particles, for example) buried in the multi-particle structure having the dielectric properties, illumination is made with a DF configuration utilizing the characteristic that an electromagnetic wave long about 10 times the particle size of the multi-particle passes through the multi-particle structure, thereby making it possible to detect a conductive material of a size smaller than other detecting means with high sensitivity.

With the configuration that the oblique irradiation is made with the terahertz illumination light being expanded to the area corresponding to the size of the sensor with the DF configuration, and the detection optical system is placed vertically above the object such as a cell sheet or the like, it is possible to keep the focus and perform a foreign matter analysis and inspection of a large area simultaneously.

By arranging a plurality of detection optical units (sensors) to form a one-dimensional sensor or a two-dimensional sensor, it is possible to expand ranges being inspectable simultaneously. Further, by arranging detection optical units each corresponding to the dimensions of the width of the electrode sheet, it is possible to perform the inspection of the entire surface in one pass.

Since the terahertz wave causes vibrations in a variety of material molecules, the material of each material can be analyzed by measuring the spectral distribution of the reflected light or scattered light from the material. In particular, in the case where the object is of the electrode sheet of the LIB, containing the moisture in the electrode material is not desirable. Therefore, the merit of enabling the analysis of moisture content is large.

By converting the specular reflected light into visible light by an EO device and detecting the position of the specular reflected light with a visible light sensor, the detection of the reflection position is possible, and an autofocus function can be provided using this data.

EXPLANATION OF REFERENCE NUMERALS

100: terahertz illumination light, 130: illumination light aperture, 140: line-shaped light portion, 170: femtosecond pulsed laser, 180: photoconductive antenna element, 200: scattered light detector, 210: specular reflection light detector, 220: scattered light detection aperture, 260: detection optical unit, 300: foreign matter particle, 310: substrate, 350: reflection plate moving direction, 400: heterodyne, 410: lock-in amplifier, 420: local oscillator, 430: attenuator, 440: band-pass filter, 450: low noise amplifier, 460: low-pass filter, 470: signal output, 500: output, 520: work moving direction, 530: upper surface reflected light, 540: lower surface reflected light, 600: EO crystal device, 610: polarizing plate, 620, 630: probe light, 640: detection light plate, 650: infrared and visible light detector, 660: scattered light, 670: specular reflected light, 700: electrode mixture layer, 701: active material, 710: collector, 720: metal foreign matter, 730: substrate, 801: nanosecond pulsed laser, 802: non-linear crystal, 1010: one-dimensional sensor, 1020: two-dimensional sensor.

The invention claimed is:

1. A device for detecting foreign matter which detects the foreign matter buried in an object being a multi-particle structure,
comprising an illumination light generating unit which generates an illumination light to be irradiated to the object; and
a scattered light detection optical system including a scattered light detecting unit which detects scattered light from the object as a signal using a light receiving element,
wherein a wavelength of the illumination light ranges from 4 µm to 10 mm, and
wherein the scattered light detection optical system is arranged at a position facing a side of the object on which the illumination light is irradiated and at an angle where a specular reflected light from an interface existing inside the object does not enter and a ratio of an amount of scattered light from the multi-particle structure to an amount of scattered light from the foreign matter is minimized.

2. The device for detecting foreign matter according to claim 1, further comprising:
a specular reflection light detecting unit which detects a specular reflected light from the object using a light receiving element; and
an analyzing unit which performs a calculation of a thickness of the object or a depth of the foreign matter contained in the object from the signal obtained by the specular reflection light detecting unit.

3. The device for detecting foreign matter according to claim 2, further comprising a focal distance adjusting unit which adjusts a focal length of each of the scattered light and the specular reflected light.

4. The device for detecting foreign matter according to claim 2, wherein the analyzing unit performs an analysis of components of the foreign matter or a detection of moisture contained in the object from the signal obtained by the specular reflection light detecting unit.

5. The device for detecting foreign matter according to claim 2, further comprising a non-linear crystal device which converts the wavelength of at least one of the scattered light and the specular reflected light,
wherein at least one of the scattered light detection optical system and the specular reflection light detecting unit includes an infrared and visible light detector.

6. The device for detecting foreign matter according to claim 2, wherein at least one of the scattered light detecting unit and the specular reflection light detection optical system includes a one-dimensional sensor or a two-dimensional sensor in which a plurality of sensors are arranged.

7. The device for detecting foreign matter according to claim 1, further comprising a smoothing processing unit which smoothes the signal obtained by the scattered light detecting unit detection optical system; and
a filter processing unit which filters the smoothed signal smoothed in the smoothing processing unit.

8. The device for detecting foreign matter according to claim 7, further comprising a manifestation processing unit which executes a differential processing of a noise removal signal obtained by the filter processing unit.

9. The device for detecting foreign matter according to claim 1, further comprising:
a heterodyne which processes a signal obtained by the scattered light detection optical system; and
a lock-in amplifier.

10. The device for detecting foreign matter according to claim 1, further comprising:
a synchronous detecting unit which processes a signal obtained by the scattered light detection optical system; and
a lock-in amplifier.

11. The device for detecting foreign matter according to claim 1, further comprising a non-linear crystal device which converts the wavelength of the scattered light,
wherein the scattered light detection optical system includes an infrared and visible light detector.

12. The device for detecting foreign matter according to claim 1, wherein the illumination light generating unit includes: a combination of femtosecond pulsed laser and a photoconductive antenna InGa electrostrictive element; a combination of nanosecond pulsed laser and a non-linear crystal device, a quantum cascade laser that generates a terahertz wave, a Schottky barrier diode that generates a terahertz wave, a Gunn diode or a TUNNETT diode.

13. The device for detecting foreign matter according to claim 1, wherein the scattered light detection optical system includes a one-dimensional sensor or a two-dimensional sensor in which a plurality of sensors are arranged.

14. A method for detecting foreign matter which detects foreign matter buried in an object being a multi-particle structure, the method comprising the steps of:
irradiating the object with an illumination light; and
detecting a scattered light from the object as a signal by using a scattered light detection optical system,
wherein a wavelength of the illumination light ranges from 4 µm to 10 mm, and
wherein the scattered light detection optical system is arranged at a position facing a side of the object on which the illumination light is irradiated and at an angle where a specular reflected light from an interface existing inside the object does not enter and a ratio of an amount of a scattered light from the multi-particle structure to an amount of a scattered light form the foreign matter is minimized.

15. The method for detecting foreign matter according to claim 14, further comprising a step of smoothing and filtering the signal of scattered light.

16. The method for detecting foreign matter according to claim 15, further comprising a step of performing differential processing on the signal subjected to the filtering.

17. The method for detecting foreign matter according to claim 14, further comprising a step of detecting a specular reflected light from the object.

18. The method for detecting foreign matter according to claim 17, further comprising a step of adjusting a focal length of each of the scattered light and the specular reflected light.

19. The method for detecting foreign matter according to claim 17, further comprising a step of performing a calculation of a thickness of the object or a depth of the foreign matter contained in the object, or an analysis of components of the foreign matter or a detection of moisture contained in the object from a signal obtained by detecting the specular reflected light.

20. The method for detecting foreign matter according to claim 17, further comprising a step of converting the wavelength of at least one of the scattered light and the specular reflected light.

21. The method for detecting foreign matter according to claim 14, further comprising a step of converting the wavelength of the scattered.

* * * * *